(12) United States Patent
Mandzsu et al.

(10) Patent No.: US 8,196,270 B2
(45) Date of Patent: Jun. 12, 2012

(54) METHODS FOR MAKING FASTENERS

(75) Inventors: Zoltan Mandzsu, Budapest (HU);
Jozsef Mandzsu, Jr., Fot (HU); Jozsef Mandzsu, Sr., Budapest (HU)

(73) Assignee: 3M Innovative Properties Company, St. Paul, MN (US)

( * ) Notice: Subject to any disclaimer, the term of this patent is extended or adjusted under 35 U.S.C. 154(b) by 1014 days.

(21) Appl. No.: 11/817,723

(22) PCT Filed: Mar. 9, 2006

(86) PCT No.: PCT/US2006/008319
§ 371 (c)(1),
(2), (4) Date: Sep. 4, 2007

(87) PCT Pub. No.: WO2006/099000
PCT Pub. Date: Sep. 21, 2006

(65) Prior Publication Data
US 2008/0140043 A1 Jun. 12, 2008

(30) Foreign Application Priority Data

Mar. 11, 2005 (HU) ..................................... 0500291
Oct. 25, 2005 (HU) ..................................... 0500970

(51) Int. Cl.
A44B 1/04 (2006.01)
A44B 11/25 (2006.01)
A44B 17/00 (2006.01)
A44B 18/00 (2006.01)

(52) U.S. Cl. ......................................... 24/446; 604/391

(58) Field of Classification Search .................. 604/386, 604/389, 391; 24/446, 448–450
See application file for complete search history.

(56) References Cited

U.S. PATENT DOCUMENTS

| 2,370,636 A | 3/1945 | Carlton |
| 2,447,374 A | 8/1948 | Smyser |
| 3,138,841 A | 6/1964 | Naimer |

(Continued)

FOREIGN PATENT DOCUMENTS
EP 1227741 8/2002
(Continued)

OTHER PUBLICATIONS

Office Action dated Apr. 30, 2008, for U.S. Appl. No. 11/530,499.
(Continued)

*Primary Examiner* — Melanie Hand

(57) ABSTRACT

There is provided a fastener for engaging with a loop fabric, comprising a base having a front surface with a multiplicity of engaging projections. At least some of the engaging projections having a top surface end and an attached end. The at least some engaging projections top surface ends form an edge angle surrounding the projections. A mantle surface extending from the top surface end edge to the attached end. Generally at least one contour line of a side view of the mantle surface is convex.

There is also provided a first method for forming a fastener, comprising:
dispersing polymer particle into a contact release surface;
transforming the polymer particles into an at least semiliquid state of a suitable viscosity for a time sufficient to transform into preform projections having contact edges;
contacting and fixing the front surface of the base with the terminal ends of at least some of the preform projections;
removing the base, thereby separating the preform projections, from the release surface;
forming engaging projections projecting from the front surface of the base.

119 Claims, 7 Drawing Sheets

U.S. PATENT DOCUMENTS

| | | | |
|---|---|---|---|
| 3,312,583 | A | 4/1967 | Rochlis |
| 3,550,837 | A | 12/1970 | Erb |
| 3,594,863 | A | 7/1971 | Erb |
| 3,770,359 | A | 11/1973 | Hamano |
| 3,922,455 | A | 11/1975 | Brumlik |
| 4,021,003 | A | 5/1977 | Buhler |
| 4,615,084 | A | 10/1986 | Erb |
| 4,794,028 | A | 12/1988 | Fischer |
| 5,092,910 | A | 3/1992 | deKok et al. |
| 5,149,573 | A | 9/1992 | Kobe et al. |
| 5,230,851 | A | 7/1993 | Thomas |
| 5,279,604 | A | 1/1994 | Robertson |
| 5,315,740 | A | 5/1994 | Provost |
| 5,380,390 | A | 1/1995 | Tselesin |
| 5,403,302 | A | 4/1995 | Roessler |
| 5,496,386 | A * | 3/1996 | Broberg et al. ............ 51/295 |
| 5,540,673 | A | 7/1996 | Thomas |
| 5,549,962 | A | 8/1996 | Holmes et al. |
| 5,591,239 | A * | 1/1997 | Larson et al. ............ 51/294 |
| 5,603,145 | A * | 2/1997 | Arakawa et al. ............ 24/442 |
| 5,679,302 | A | 10/1997 | Miller |
| 5,792,411 | A | 8/1998 | Morris |
| 5,879,604 | A | 3/1999 | Melbye |
| 5,884,374 | A | 3/1999 | Clune |
| 5,900,350 | A | 5/1999 | Provost |
| 5,953,797 | A | 9/1999 | Provost |
| 6,007,527 | A | 12/1999 | Kawaguchi |
| 6,035,498 | A | 3/2000 | Buzzell |
| 6,039,911 | A | 3/2000 | Miller |
| 6,044,525 | A | 4/2000 | Sastre |
| 6,054,091 | A | 4/2000 | Miller |
| 6,080,347 | A | 6/2000 | Goulait |
| 6,162,040 | A | 12/2000 | Clune |
| 6,180,205 | B1 | 1/2001 | Tachauer |
| 6,206,679 | B1 | 3/2001 | Provost |
| 6,248,276 | B1 | 6/2001 | Parellada |
| 6,287,665 | B1 | 9/2001 | Hammer |
| 6,357,087 | B1 | 3/2002 | Takizawa |
| 6,444,080 | B1 | 9/2002 | Mandzsu |
| 6,470,540 | B2 | 10/2002 | Aamodt |
| 6,489,003 | B1 | 12/2002 | Levitt |
| 6,569,494 | B1 | 5/2003 | Chambers et al. |
| 6,588,073 | B1 | 7/2003 | Zoromski et al. |
| 6,592,800 | B1 | 7/2003 | Levitt |
| 6,598,276 | B2 | 7/2003 | Shepard |
| 6,606,768 | B2 | 8/2003 | Henry |
| 6,627,133 | B1 | 9/2003 | Tuma |
| 6,660,121 | B2 | 12/2003 | Harvey |
| 6,669,745 | B2 | 12/2003 | Prichard et al. |
| 6,669,884 | B1 | 12/2003 | Tuma |
| 6,678,924 | B2 | 1/2004 | Murasaki |
| 6,681,457 | B2 | 1/2004 | Okawa |
| 6,692,674 | B1 | 2/2004 | Kurtz, Jr. et al. |
| 6,708,378 | B2 | 3/2004 | Parellada |
| 6,736,804 | B1 | 5/2004 | Robertson |
| 6,752,700 | B2 | 6/2004 | Duescher |
| 6,835,256 | B2 | 12/2004 | Menzies et al. |
| 6,962,635 | B2 | 11/2005 | Tuman et al. |
| 7,032,278 | B2 | 4/2006 | Kurtz, Jr. |
| 7,044,989 | B2 | 5/2006 | Welygan et al. |
| 7,168,139 | B2 | 1/2007 | Seth |
| 7,374,706 | B2 | 5/2008 | Schulte |
| 7,811,272 | B2 | 10/2010 | Lindsay |
| 2001/0052170 | A1 | 12/2001 | Aamodt |
| 2002/0104202 | A1 * | 8/2002 | Henry et al. ............ 24/306 |
| 2002/0116799 | A1 | 8/2002 | Martin |
| 2003/0009144 | A1 | 1/2003 | Tanzer |
| 2003/0087059 | A1 | 5/2003 | Jackson |
| 2003/0104137 | A1 | 6/2003 | Schulte |
| 2003/0106188 | A1 | 6/2003 | Armela |
| 2003/0106189 | A1 | 6/2003 | Okawa |
| 2003/0131453 | A1 | 7/2003 | Clarner et al. |
| 2004/0031130 | A1 | 2/2004 | Clarner |
| 2004/0068848 | A1 | 4/2004 | Ausen |
| 2004/0094860 | A2 | 5/2004 | Jens |
| 2004/0119192 | A1 | 6/2004 | Tuma |
| 2004/0222551 | A1 | 11/2004 | Provost et al. |
| 2004/0261231 | A1 * | 12/2004 | Seth et al. ............ 24/452 |
| 2005/0003146 | A1 | 1/2005 | Spath |
| 2005/0039313 | A1 | 2/2005 | Melbye |
| 2005/0148984 | A1 * | 7/2005 | Lindsay et al. ............ 604/387 |
| 2005/0241119 | A1 | 11/2005 | Efremova |

FOREIGN PATENT DOCUMENTS

| | | |
|---|---|---|
| EP | 1287757 | 3/2003 |
| GB | 2279106 | 12/1994 |
| HU | 217379 | 4/1995 |
| HU | 215897 | 6/1998 |
| HU | 222449 | 5/1999 |
| HU | 222516 | 7/2001 |
| JP | 63-203103 | 8/1988 |
| JP | 10-057117 | 3/1998 |
| WO | WO 93/00025 | 1/1993 |
| WO | WO 98/29003 | 7/1998 |
| WO | WO 01/33989 | 5/2001 |
| WO | WO 01/33989 A1 | 5/2001 |
| WO | WO 0133989 A1 * | 5/2001 |
| WO | WO 01/49776 | 7/2001 |
| WO | WO 0149776 A2 * | 7/2001 |
| WO | WO 02/091870 | 11/2002 |
| WO | WO 03/039868 | 5/2003 |
| WO | WO 03/059110 | 7/2003 |
| WO | WO 2006/099000 | 9/2006 |
| WO | WO2008/033816 | 3/2008 |

OTHER PUBLICATIONS

Office Action dated Aug. 9, 2010 for U.S. Appl. No. 12/617,276.
Office Action dated Oct. 30, 2008 for U.S. Appl. No. 11/530,499.
Office Action dated May 14, 2009 for U.S. Appl. No. 11/530,499.
PCT International Search Report, International Application No. PCT/US2007/075783, dated May 26, 2011.

* cited by examiner

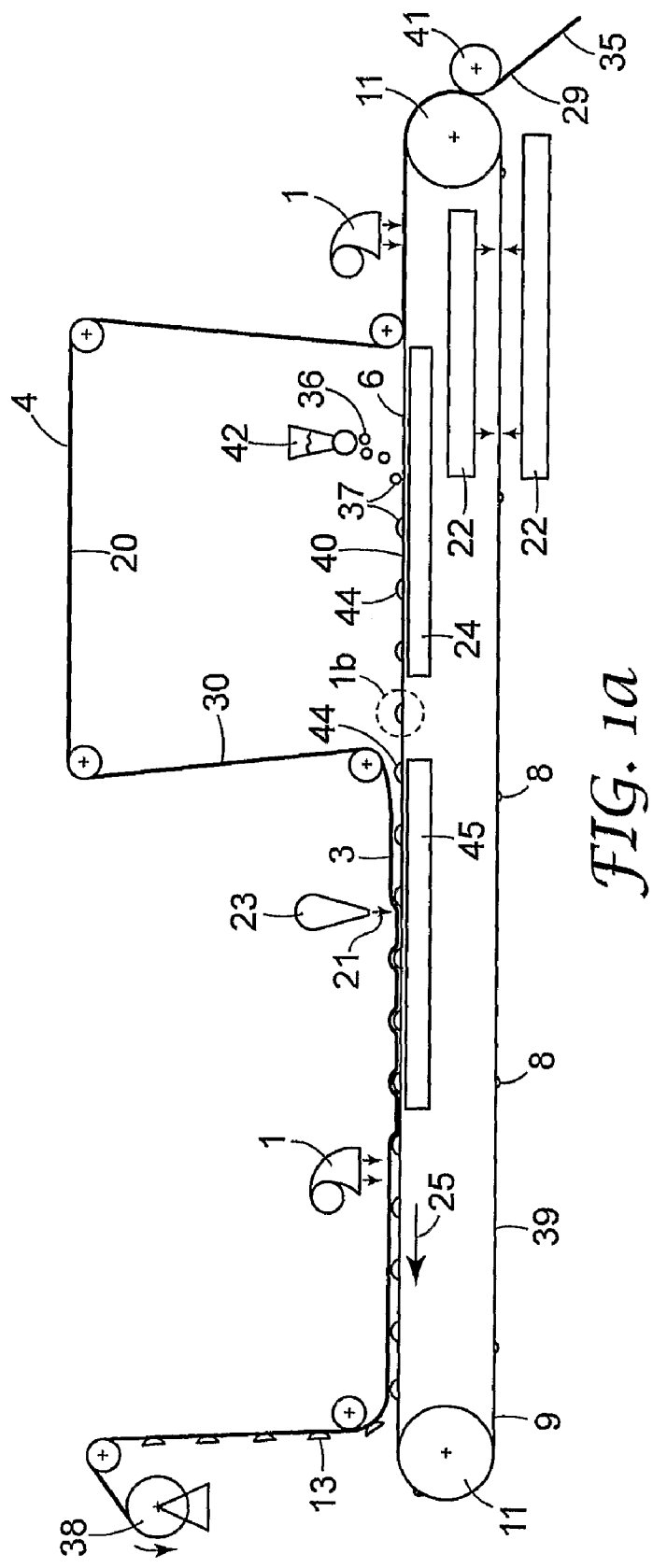
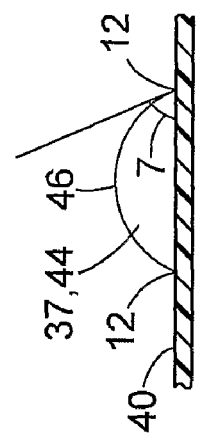
FIG. 1a
FIG. 1b

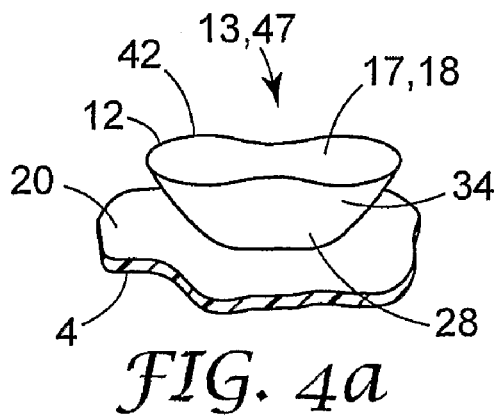
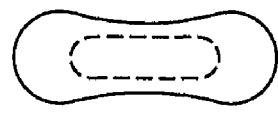
FIG. 4b
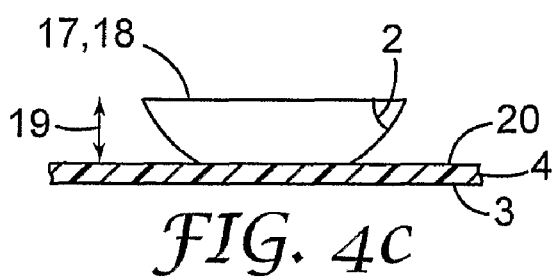
FIG. 4a
FIG. 4c
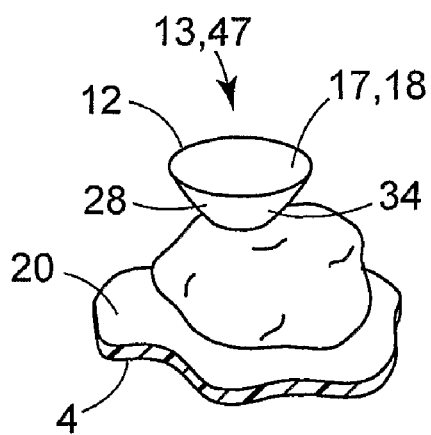
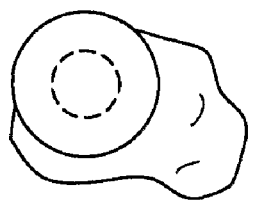
FIG. 5b
FIG. 5a
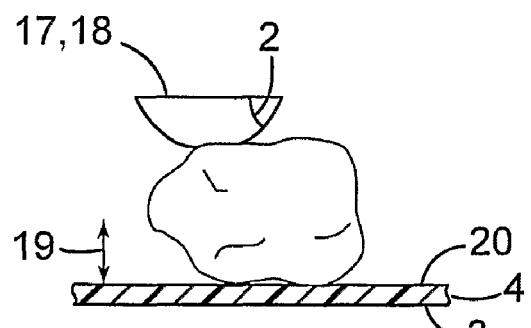
FIG. 5c

METHODS FOR MAKING FASTENERS

CROSS REFERENCE TO RELATED APPLICATIONS

This application is a national stage filing under 35 U.S.C. 371 of PCT/US2006/008319, filed Mar. 9, 2006, which claims priority to HU P0500291, filed Mar. 11, 2005 and HU P0500970, filed Oct. 25, 2005, the disclosure of which is incorporated by reference in its/their entirety herein.

TECHNICAL FIELD

The present invention relates to methods of manufacturing fasteners, particularly male components for fasteners of the touch-and-close type, also known as hook-and-loop type fasteners.

BACKGROUND OF THE INVENTION

It is common to use certain types of hook-and-loop type mechanical fasteners for fixing disposable diapers, training pants and incontinence garments around a wearer. One approach is a thin, molded male fastener with low loft loop materials, preferably nonwoven, fabrics as the female components. For these uses generally low cost, soft touch, appropriate strength and increasing stretch in the waistline are important. The word "loop", as used in this document, also includes low lying, free sections of fabric filaments, such as those of a thin nonwoven fabric, capable of mechanically engaging with a male fastener component, the usage of the word being in accordance with its current general use in the art of separable fasteners.

Hooks can be directly molded as disclosed for example in U.S. Pat. No. 5,315,740, assigned to Velcro, which discloses molded hooks with low displacement volumes so that it needs only to displace a small volume of loop fabric in order to engage therewith. The patent discloses a re-entrant hook, i.e., whose tip-portion curves over and down toward the base sheet from the upper end of the hook to define a fibre-retaining recess on the underside of the hook.

It is also known to cap molded stems on webs. Mushroom-shaped engaging projections obtained by this process are disclosed in U.S. Pat. No. 5,679,302 and U.S. Pat. No. 5,879,604 in which an extruded polymer layer is pressed against a mold with mold cavities, the cavities producing projecting stems, integral with the base. The terminal ends of the stems are then deformed with a heated pressure roller, forming the loop engaging projections. U.S. Pat. No. 6,054,091 discloses a similar method in which, however, the heated deforming surface gives an essentially lateral deformation to the stems during the deformation thereby forming re-entrant, J-shaped hooks with flat top portions. The solution of U.S. Pat. No. 6,627,133 differs from the previous ones in that the stemmed web, to be capped with a heated pressure roller, is manufactured with the method of U.S. Pat. No. 6,287,665, i.e., with a special mold constituted by a cylindrical printing screen. All documents mentioned in this paragraph are similar in that they flatten preformed stems by a hot roll.

U.S. Patent Application 2004/0031130A1 discloses a method in which a product, comprising a polymer base and stems integral with and projecting from a base is extrusion-molded with a mold roll having a multiplicity of sophisticated mold cavities. The distal ends of the stems are then heated and melted while their feet are kept cold and solid. The melted ends are then flattened with a deforming surface. The same approach, i.e., pre-heating and successively flattening stems, appears in U.S. Pat. No. 6,592,800, U.S. Pat. No. 6,248,276 and U.S. Pat. No. 6,708,378, the latter ones also disclosing capping with a rough contact surface, creating roughened flat tops of engaging projections.

U.S. Pat. No. 6,039,911 discloses a stem-deforming apparatus comprising a long variable nip, e.g., a pair of co-operating conveyors, which gradually compressively deform the stems, unitary with the base.

U.S. Pat. No. 6,470,540 uses a hot extruded layer for deforming stems, which results in semi-spherical mushroom heads.

In U.S. Pat. No. 3,550,837 a male fastener member is described whose each engaging projection is constituted by an irregularly shaped granule with a special multifaceted surface, adhesively adhered to the base. The fastener is suitable for securing a flap of a disposable carton against opening. Engaging is provided by the granules comprising a number of tiny flat planes forming a multifaceted surface.

In U.S. Pat. No. 3,922,455 nibs of various shapes are grafted onto linear filaments, the linear filaments, protruding from a base, forming the engaging elements of a male fastener component.

In PCT publication WO 01/33989, particles are, with a scatter head of a scatter coater, randomly scattered, and fixed, onto a base. Each engaging projection is constituted by several agglomerated particles, though some individual particles may also be left present.

It was therefore an object of the present invention to provide low-cost male mechanical fasteners with advantageous properties. It was another object of the present invention to provide commercially attractive alternatives to the mechanical male fastener systems available so far and methods for making them.

BRIEF DESCRIPTION OF THE INVENTION

The present invention provides a fastener for engaging with a loop fabric, comprising a base having a front surface with a multiplicity of engaging projections at least some of the engaging projections having a top surface end, where the at least some engaging projections top surface ends form an edge angle surrounding the projections, an attached end and a mantle surface extending from the top surface end edge to the attached end; at least one contour line of a side view of the mantle surface being strictly convex from a top surface edge to the attached end.

The present invention furthermore provides a fastener for engaging with a loop fabric, comprising a base having a front surface with a multiplicity of engaging projections at least some of the engaging projections having a top surface end and an attached end, which attached end is fused to the front surface of the base and the top surface forming an edge at least partially surrounding the projection.

The present invention furthermore provides fastener for engaging with a loop fabric, comprising a base having a front surface with a multiplicity of randomly distributed engaging projections at least some of the engaging projections having a top surface end and an attached end wherein at least some neighboring engaging projections, of the at least some engaging projections, are merged along adjacent side edges, forming a merged engaging projection.

The male mechanical fasteners of the invention are preferably capable of engaging with thin or ultra thin loop fabrics, especially nonwoven fabrics. Due to their shape the fasteners may be gently contacted with loop fabrics. If a moderate shear load is applied, the edge of the projections, being essentially in the plane of the top surface and forming an edge angle, can readily enter the loop fabric without a need for displacing a substantial volume of the loop fabric.

The present invention furthermore provides a fastener for engaging with a loop fabric, comprising a base having a front surface with a multiplicity of engaging projections, wherein the at least some engaging projections have no stem.

The invention furthermore provides method for forming a fastener, comprising:
- providing a multiplicity of suitable polymer particles;
- providing a base with a front surface;
- providing a contact release surface of a suitable surface energy;
- dispersing, on the contact release surface, the multiplicity of polymer particles thereby forming separate preform projections sitting on, and projecting from, the release surface to corresponding terminal ends;
- transforming the polymer particles, dispersed on the contact release surface, into an at least semiliquid state of a suitable viscosity, at least some of said particles being in contact with the contact release surface for a time sufficient to transform into preform projections having contact edges influenced by the surface energies of the polymer particles and the contact release surface;
- contacting and fixing the front surface of the base with the terminal ends of at least some of the preform projections;
- removing the base, thereby separating the preform projections fixed thereto, from the release surface; and
- thereby forming engaging projections projecting from the front surface of the base.

The present invention furthermore provides a method for forming a fastener, comprising:
- providing a multiplicity of suitable thermoplastic particles;
- providing a base with a front surface;
- randomly dispersing and adhering, on the base front surface, the multiplicity of polymer particles thereby forming separate projections attached and projecting from the base front surface to corresponding terminal ends;
- providing a deformation means having a contact surface;
- contacting the terminal ends of the projections with the contact surface of the deformation means to deform the terminal ends so that they form a rim comprising an acute edge angle (the process of transforming the polymer to form a acute contact angle is also termed sharpening) thereby forming engaging projections.

In various preferred embodiments, the male mechanical fastener materials and the corresponding methods of the invention may offer the following advantages:
- a male mechanical fastener with a pleasant touch and/or skin friendliness;
- the possibility of selecting the material of the front surface, or the entirety, of the base independently from that of the engaging projections, this feature inherently providing the further advantageous possibilities of providing a fastener having alternatively;
- hard (thereby strong) engaging projections in combination with a soft (thereby skin friendly) base,
- an (elastically) extensible base,
- an inexpensive base, due to the base having been made separately with efficient methods optimized to forming a base,
- a base having a high tensile strength,
- a base being highly flexible thereby skin-friendly,
- a base being very thin thereby skin-friendly and inexpensive,
- a base having a back surface with a suitable compatibility for bonding to other materials,
- the ability to freely and easily vary the material of the base thereby modifying the appearance and features of, i.e. re-configuring, the manufactured fasteners.

Generally the methods of the invention are capable of forming an inexpensive male fastener product with advantageous properties. In particular, the male fasteners have a novel structure and appearance compared to prior fasteners. The corresponding manufacturing methods provide a great variety of different fasteners at low cost.

The methods of the invention are also capable of forming a novel fastener providing engagement with low loft loop fabrics, especially ultra-low loft nonwoven fabrics, the engagement preferably having a high shear strength in all directions (isotropic fastener).

The male mechanical fasteners of the invention can also be used in disposable diapers. In a preferred embodiment the fastener is capable of engaging with the nonwoven outer shell of a diaper strongly enough to securely keep the soiled diaper in a folded state. Further, preferably the engagement with the nonwoven outer shell of a diaper is strong enough to secure the diaper around a wearer during use, thereby making a separate frontal tape, of a special loop fabric, in the landing zone unnecessary, which can provide considerable cost saving.

The male mechanical fasteners of the present invention can also be used to form a so-called back-to-back wrapping tape that has the fastener of the present invention on one face thereof thereby offering such new possibilities, deriving from the invention, such as an inexpensive, highly flexible still strong, very thin or easily cut wrapping tape. In a preferred embodiment, the wrapping tape can be easily written upon with a pen. In another preferred embodiment the wrapping tape may be elastically stretchable and can be advantageously used for packaging or technical (e.g. cable wrap) applications.

DETAILED DESCRIPTION OF THE INVENTION

The present invention provides a fastener for engaging with a loop fabric. The fastener comprises a base having a front surface with a multiplicity of engaging projections. At least some of the engaging projections having a top surface end, where at least some engaging projections top surface ends form an edge angle surrounding the projections. Opposite the top surface end is an attached end which is attached to the front surface of the base. There is a mantle surface extending from the top surface end edge to the attached end. The mantle surface in some embodiments has at least one contour line of a side view of the mantle surface that is strictly convex from a top surface edge to the attached end.

The present invention furthermore provides a fastener for engaging with a loop fabric, comprising a base having a front surface with a multiplicity of engaging projections at least some of the engaging projections having a top surface end and an attached end, which attached end is fused to the front surface of the base and the top surface forming an edge at least partially surrounding the projection.

The present invention furthermore provides fastener for engaging with a loop fabric, comprising a base having a front surface with a multiplicity of randomly distributed engaging projections at least some of the engaging projections having a top surface end and an attached end wherein at least some neighboring engaging projections, of the at least some engaging projections, are merged along adjacent side edges, forming a merged engaging projection.

The male fastener materials can be obtained in a first preferred method in which the polymer particles are first fixed to the base and then capped or flattened by contacting them with a deformation surface. In a preferred second method of the invention the polymer particles are first deposited on a release surface, formed into perform projections having acute contact angles with respect to the release surface, transferring the perform projections to a base thereby forming engaging projections with acute edge angles.

Accordingly, the first preferred method for manufacturing a male fastener component generally comprises the following steps:

providing a base with a front surface;
providing particles of thermoplastic material;
randomly bringing and fixing the particles to the front surface thereby forming a multiplicity of thermoplastic projections or particles extending from the front surface to corresponding terminal ends where at least the terminal ends of the formed projections constituted by the particles that were brought and fixed;
providing a deforming means having a contact deformation surface; and
contacting the terminal ends of the projections with the contact deformation surface for a suitable period of time thereby deforming the terminal ends to form engaging projections of the fastener where during the contacting the terminal ends of the projections are heated above a softening temperature while the front surface is generally kept cold enough to provide for suitable stability of the both the base front surface and the portions of the projections adjacent to the base front surface. The top terminal end is then cooled. The terminal end of the projection can form an essentially flat top surface where the top surface at least partly overhangs the base. During the contacting of the heated terminal end with the contact deformation surface, a contact area is created bordered by a contact line. Along at least a part of the contact line the heated terminal end is provided with an acute contact angle.

The contact angle is influenced by the surface energies (i.e. surface tension) of the contact surface and of the material heated terminal end thereby the formed flat top surface being bordered, at least partly, by an edge having an angle influenced by the acute contact angle.

The base used in the first, or second, method of the invention can be any suitable continuous or discontinuous base web such as a porous or nonporous polymer film, a laminate film (multilayer), a nonwoven web, a paper web, a metal films and foils or the like. The base could be modified by any known method such as by being printed, embossed, flame treated, laminated, particle coated, colored, or the like. The film could also be structured such as having projections or valleys molded into the base which could be used as ripstops, tear propagation lines or other features, which could be on the front or rear face of the base. A polymer film used as a base can be oriented or unoriented although essentially unoriented films are preferred in the first method. The base can be from 5 to 100 microns thick. The word "particle", as used herein, refers to a solid, liquid or semi-liquid particle, including, for example, granules, pellets, powders and droplets. The front surface of the base can be smooth or rough. For example the front surface can be roughened with particles previously scattered and fixed thereon. The particles should be brought and fixed on the base 4 in a way that at least the terminal ends of the projections can be formed from the particles. Projections can consist completely of the particles without any further modification of said particles. For bringing and fixing the particles to the (smooth or roughened) front surface, several methods are taught, e.g., random scattering and adhering, for example, in the cited PCT publication WO 01133989, the entire disclosure of which is hereby incorporated by reference.

The deforming means used in the first method of the present invention are well known and include, but are not restricted to, hot rolls or plates, preheating means combined with a roll and elongated variable nips. The contact surface of the deforming means can be smooth or suitably structured or roughened, e.g., grooved, as known from the art. The heating of the terminal ends of the particles can be provided by, e.g., a pre-heater or the contact surface of the deforming means or both. The skilled person will be able to select a way of keeping the base and, also, the attached ends of the projections cold enough, thereby solid enough, to prevent undesired deforming thereof. One exemplary way to achieve this can be keeping the back of the base in contact with a cooled surface. The top surface of the deformed particles, i.e. the projections, can be formed by a contact deformation surface that can be smooth but can also be somewhat roughened, e.g., sandpaper-like or grooved. However, the contact deformation surface preferably will be essentially flat, even if they may not be planar in the true geometrical sense. Post treatments of the perform projections could however be used that would make the top surface not essentially flat, such as using non-contact heat treatment. Surface energies, known to influence contact angles, include the surface energies of the particles and of the contact surfaces and their relative interfacial energy.

If there is essentially no molecular orientation of the particles or formed projections the contact angle is mainly determined by the surface energies of the particle polymers and the contacting surface. The contact angle is furthermore influenced by the contact time, which should be selected appropriately. Subsequent cooling of the projections preserves the edge angles of the projections and can be selected, for example, from ambient cooling, contact cooling, cooling with air etc.

In the first method of the present invention the deformed projections, i.e. the engaging projections, preferably have flat tops making the fastener formed smooth to the touch. The material forming the base can be independently selected from the material forming the particles. The process parameters are very flexible. Using different particles of different materials, shapes and/or sizes, will result in a different products. Also mixtures of particles of different properties could be used. The density of the projections can be varied during the process with no additional capital costs (e.g. there is not any need for changing molds). Also by choosing a thin base, e.g. a suitable film, a thin fastener can readily be made, the thickness can be further decreased by using small particles resulting in small projections which may also function especially well with thin loop fabrics. The shape of these engaging projections are advantageous for engagement with low loft, thin fabrics, e.g., even ultra thin spunbond nonwovens. The symmetry of the method and the deformed projections also can provide an isotropic fastener.

When the first method of the present invention is conducted at a low speed there is more time for the surface tension effects to create acute contact angles so that the engaging projections have more acute edge angles. The first method can be run slower, for example, by using an elongated variable nip that gradually compressively deforms the terminal ends of the particles or projections.

The deformed projections can be solidified, in this case by cooling, in their most compressed state. It is also possible that after the deformed projections are in their most compressed state and before the deformed projections are in their final solidified state the deformed projections are somewhat lengthened by stretching when removed from the deforming surface The terminal ends of the deformed projections can be stretched from the base by opening a nip while they are still attached to the deforming surface, thereby causing the projections to get slimmer in their middle section.

When many small projections are desired it is preferable to form at least some deformed projections comprising one particle per deformed projection. This makes the process less expensive than forming the projections from multiple small particles as less expensive larger particles can be used to form the projections. This can be inexpensively achieved by uniformly scattering suitable polymer powder particles over a moving base at a suitable distance to provide the projections or particles.

The edge angle between the top of the deformed projection and the mantle surface may vary over a broad range. A too sharp edge angle, however, may weaken the fastener, probably due to weakening the overhanging rim by making it too thin, subject to bending or breaking. Therefore it is preferable that the contact angles are between, 20° and 85° and more preferably between 30° and 80°. This would be the range of individual contact angles for most of the deformed top surfaces of the projections. A skilled person can achieve this by suitably selecting the conditions in the method, such as the materials of the particles and the contact surface, the contact period time and other details of the contact deformation step.

It is preferable if at least some engaging projections are provided with a side view which strictly tapers from the top surface or top surface edge to the attached end at the front surface of the base. This type of engaging projection is particularly possible to form with the second embodiment method. Strictly tapering means that the nearer the engaging projection gets to the base, the narrower the projection becomes. For example, a cylinder is not a strictly tapering shape. This type of tapering will pull engaged fibres down to the front surface of the base when a shear load is applied to the fastener without the fibres being caught at a nontapered portion displaced from the front surface of the base. Thus the torque on the engaging projection is minimal so the base can be weaker, i.e., can be cheaper, more flexible, more skin friendly, thinner etc. Furthermore, the fastener may have a relatively large surface area formed by the projection tops, making the fastener smooth to the touch, while also having a relatively low total surface area of the projection attached ends connected to the base, increasing the flexibility and skin-friendliness of the fastener. The engaging projections 13 can also be characterized by a ratio of the perimeter of area 17, 18 of the engaging top to the height 19 of the engaging projection, which is generally 1.1 to 50, and is preferably 1.2 to 20 or 4.5 to 20. The engaging projection 13 also generally forms an overhanging rim 100 as shown in FIG. 3c, which generally is the difference between the top surface area 17, 18 and the area of the attached end 102.

The projection top surface has an area and the projection attached end has an area where it is attached to the front surface of the base. The ratio of the average top surface area to the average attached end area is from 1.56 to 25. The projections also can have a volume of from 0.0000335 $mm^3$ to 33.5 $mm^3$.

In both of the invention methods, during the forming of the heated ends of the preform projections (second method) or the deformation of the projections or particles (first method), some preform projections or particles can unify with other, neighboring, preform projections or particles. "Unify" means that two neighboring preform projections or particles fuse or merge into a single preform or engaging projection. It is possible that only preform projections or particles portions near the tops fuse, their attached ends remaining separate, but it also possible that the attached ends unify with the neighboring partner preform projections or particles. It may be preferred that only a part, of the preform projections or particles unify, while the rest remain separate, this provide a variety of engaging capabilities. A fastener with some unified engaging projections may provide an enhanced shear strength with respect to certain loop fabrics, e.g. low loft loops such as used in diaper landing zones. The cause of this phenomenon appears to first be that the elongated (in top view) shape of the new engaging projection, formed by the unification, may resist a higher torque normal to its elongated dimension. Secondly the edge angles of one of the partner merged projections, farthest from the partner the merged engaging projection, has edge angles that appear to be made more acute by the unification. It is speculated that during the unification that the polymer material of two partner projections moves from the projections remote edges toward their new common centre, due to cohesion, which leaves a so-called receding, decreased, contact angle at the outer edge portions, farthest from the centre or the contact line of the two partner projections. This allows one further way to modify the engaging performance relative the particular intended engaging loop. The unifying of neighboring projections, can be easily and inexpensively achieved and controlled by adjusting some manufacturing operational parameters, like the dosing rate of particles, or by using particles of different size- and/or melt-properties. By increasing the density of the preform projections or particles, a point occurs where the unifying phenomenon increases. This is influenced by the kind, and the shape of the particles. Using less spherical, more irregular particle, results in an increase in unification of the particles.

Molecularly unoriented thermoplastic polymers are preferred for attaching the particle to the base in the first embodiment method. Therefore it is preferable if, in the first method, the provided thermoplastic particles are unoriented particles, which can be one or more types of particles selected from a group including a) granules of a powder made with size reduction from pellets, b) granules from a reactor powder, c) granules from a precipitated powder, d) droplets.

In the first method the fixing of the particles to the front surface of the base includes keeping the particles, brought to the front surface, at least partly, at a temperature above their softening temperature.

Reactor powder means polymer powder taken from a polymer manufacturing reactor, before pelletizing. Granules from a reactor or precipitated powder, as used herein, also include granules, of such powder, further size-reduced. Droplets may be solid or not, when provided, brought and fixed to the front surface. Softening of the particle as they are attached to the base can further decrease any residual orientation in the particles.

A variation of the first method, is one where particles of a first thermoplastic material and particles of a second thermoplastic material are provided where the first thermoplastic material has:

a) a higher melt flow rate than that of the second thermoplastic material or b) a lower Vicat softening temperature than that of the second thermoplastic material or c) both a higher melt flow rate and a lower Vicat softening temperature than those of the second thermoplastic material.

Preferably the first thermoplastic polymer, being easier to melt, constitutes the top of the engaging projection while the lower portion comprises the second more difficult to melt polymer. This allows a separation of the deforming effects. Such composite engaging projections can be made, for example, with sequential scattering, over the base, of the two different polymer powders, preferably on a tilted base, as is taught in the cited PCT publication WO 01/33989, the substance of which is incorporated by reference in its entirety.

A second preferred method for manufacturing a male fastener component generally comprises the steps of:
 providing a base with a front surface;
 providing particles of polymer material;
 providing a forming contact release surface of a suitable surface energy;
 dispersing, on the contact release surface, a multiplicity of the polymer particles;
 bringing the polymer particles into an at least semi-liquid or softened state of a suitable viscosity, providing preform projections (preform projection signifies a projection that to at least some extent has been preformed into the shape of the final engaging projection at the engaging end) sitting on and projecting from the release surface to corresponding terminal ends. The preform projections along their edges contacting the contact release surface will form contact angles, which contact angle is influenced by the surface energies of the polymer particles and the contact release surface. The polymer particles are maintained in a semiliquid state for a suitable period of time so that they form an acute contact angle at least a portion of their edges contacting the contact release surface;
 the preform projections can then be at least partially solidified for contacting and fixing to the front surface of the base with the terminal ends of at least some of preform projections, while essentially maintaining the shape of the edge formed by the contact release surface;
 the preform projections are then further solidified sufficient to separate and remove the preform projections from the contact release surface thereby forming engaging projections attached to the base. These formed engaging projections project from the front surface of the base to flattened tops, which tops were formed on the contact release surface. The flattened tops at least partially overhang the base forming a rim, and are bordered, at least partly, by an edge having an angle which is influenced by the acute contact angle.

With the second method suitable particles for making a fastener are capable of being in a liquid or semiliquid (i.e., softened or suitably pliable) state; and capable of becoming solid. The particles can be, for example, droplets of liquid suspensions etc., solidifiable by irradiation, or they can be thermoplastic particles, as described above for the first method. The base can be any suitable base, e.g., a sheet-form base, e.g., a film, as described above in reference to the first embodiment method.

The skilled person, familiar with the field of surface energy, surface tension and wetting, can select a combination of a suitable polymer for the particles and a contact release surface of a suitable surface energy, and also select particles having a suitable viscosity at the temperature of the contact release surface that will wet the contact release surface within a suitable time. The surface energy of the contact release surface may be formed by known materials and methods, such as siliconized surfaces, flourochemicals, corona discharge, flame or the like. The contact release surface must be able to release the particular polymer particles used, semi-liquefied and solidified. It is known that certain release surfaces can release certain polymers but are unable to release other polymers. For example, a polyethylene release surface can release suitable polypropylene particles but can not release certain polyethylene particles as they tend to weld or fuse to each other. The word "release" as used herein refers to the phenomenon where the particles are detached from the contact release surface without (unacceptable) damage or loss of material of the particles or preform projections. The contact release surface can be smooth or suitably structured or roughened, e.g., grooved, as known from the art. Dispersing of the particles onto the release surface can be performed in any suitable way, for example, by scattering the particles with a scatter unit. The particles should be dispersed at a rate per unit surface area so that they form preform projections where one particle can form one preform projection, which may merge as discussed above. The particles can be brought into the at least semi-liquid state before, during and/or after dispersing of the particles onto the contact release surface. "At least semi-liquid" means liquid or semi-liquid. A suitable way of liquefying will depend on the properties of the selected polymer, and can include, for example, heating, thinning, solving, emulsifying, dispersing etc.

A solidity (degree or extent of solidification) suitable for contacting and fixing the preform projections on the contact release surface with the front surface of the base can be decided by the skilled person, depending on the particular circumstances. It will usually, but not necessarily, mean a more solid state than the one in which the preform projections have been formed on the contact release surface. Preferably the preform projections should be solid enough to keep, at least partly, their shape while being contacted with the front surface of the base. It usually primarily means keeping at least a minimum free height and also a suitable edge angle of the preform projections. Setting the necessary solidity in the preform projections will be material-dependent, and can include cooling, drying, heating, crosslinking, curing, chemical treatment etc. The preform projections of suitable solidity, sitting on the contact release surface, can be covered by the base front surface such that the front surface of the base can contact and fix with the preform projection terminal ends. The terminal ends are the ends farthest from the contact release surface. Before contacting with the front surface of the base, the preform projections can be provided, or supplemented, with further added dispersed particles or the like, which will attach to the preform projections. It is possible that the front surface of the base is contacted with the preform projections when the preform projections are in a semiliquid state. In this case it is possible that after the contacting, and before a final solidification, the preform projections are somewhat lengthened by stretching while the preform projections are removed from the release surface thereby causing the preform projections to get slimmer in their middles. A skilled person can also choose a base flexible enough to permit contacting preform projections of possibly non-uniform heights. The front surface of the base can be smooth but it can also be suitably rough, for example roughened with particles or projections previously scattered and fixed on the base. The fixing of the terminal ends of the preform projections to the front surface of the base can be obtained for example by, adhering with an added adhesive, crosslinking with ultraviolet irradiation, or it can utilize the inherent adhesion of the contacting materials (the base front surface or the preform projections) or fusing. Fixing with fusing will be discussed in detail later herein. While fixing, care should be taken in order that the free overhangs or rims, and the actual heights of the preform projections are sufficiently preserved. For example, an exaggerated sinking or compression of the projections into the front surface of the base should be avoided. The proper solidity of the preform projections and the base, suitable for a separating and removing both from the release surface can be decided by the skilled person, depending on the particular circumstances. The solidity of the preform projections when they are removed from the release surface will usually, but not necessarily, be a more solid state than when they are initially contacted with the front surface of the base. Preferably the preform projections should be solid enough to keep, at least partly, their shape during the separation from the release surface. It usually primarily means keeping a suitable overall shape, with particular respect to the edge angle formed, but preserving a suitably strong bond with the front surface of the base is also an important factor. The base generally should be solid enough to keep its form and separate the preform projections from the release surface. The flattened top surface as formed can be smooth but can also be somewhat roughened, e.g., sandpaper-like or grooved, as known from the art. The top surface structure will be determined by the contact release surface, which generally will be essentially flat, even if naturally not planar in the true geometrical sense. Post treatments could however be used that would make the top surface not essentially flat, such as a noncontact heat treatment. Also it is possible that the contact release surface are not flat that can form top surfaces that are a reflection of the contact release surface on which it was formed.

An advantage with the second method is that the attachment end of the preform projections is less likely to be affected by long contact times with the contact release surface as there is no pressure on the attached end. That opens a possibility of letting the surface energies work for a longer time, e.g., with a lengthened release conveyor in a production line. In other words the beneficial mechanical effects of the surface tensions forming the flattened ends, do not have to interfere, or "compete", with mechanical effects originating from an already attached end. A further advantage is that, independently of the sizes of the particles or preform projections similar contact angles can be obtained for all projections. In other words the projections all are in contact with the release surface for the same time period and under the same conditions, which is not the case if they where already attached to a base and at different heights, depending on the particle size, when contacting a deforming release surface in the first embodiment method, which gives this second embodiment method a high tolerance to particles of a varied sizes. Further significant cost savings, and simplification, are achieved by making the deformation apparatus unnecessary. Line speed and running width of the manufacturing line can probably be greater than ever before, with lower costs. A further advantage is that non-thermoplastic polymers, potentially having, e.g., better mechanical features, could be used.

Specific forms of the second method, having various advantages are possible, as will be described If small numerous projections are advantageous it is preferable if, in the second method, at least some of the separate preform projections comprise exactly one polymer particle per preform projection.

It is preferable if, in the second method, at least some of the preform projections are provided with contact angles of between 10° and 85°, preferably 30° and 80°. This would be the range of contact angles for most of the individual preform projections. For a preferred embodiment this range would be the mean contact angle for the preform projections.

It is preferable if, in this second method as in the first method, at least some engaging projections are provided with a shape in which, in each side view thereof, the engaging projection strictly tapers (preferably is strictly convex) from the flattened top or top edge to the front surface of the base. This is usually very easy to achieve by this method which typically creates semi-lenticular preform projections, like water drops sitting on a suitable surface. This is a great advantage of this method. Again with this method some preform projections may be unified with other, neighboring, preform projections. The reason for this is similar to what was explained earlier. In this second method, non-thermoplastic and thermoplastic polymer particles can be used, the selection being based on necessary strength, required surface energy, cost etc. Using thermoplastics, however, has some advantages specific to this second method, which may not be obvious. First using thermoplastic particles, and softening them after their delivery, will generally ensure that any residual molecular orientation will generally be released from the preform projections, at least where in contact with the contact release surface. Secondly, if the particles are thermoplastic, the viscosity of the liquefied or at least semi-liquefied material forming the preform projections can be controlled, e.g., fine-tuned (e.g. adjusted and/or optimized) on-line, exactly, easily, cheaply and reversibly by its temperature. The viscosity has a direct influence on the extent to which the surface energies, of and between the preform projections and the contact release surface, affect the formed contact angles. By adjusting the viscosity by appropriately selecting temperature and heating time the edge angle of the final engaging projections can be fine-tuned on-line, at no added cost. The second method used with thermoplastic particles, can result in inexpensive, formed fasteners with the flexibility of adjusting the form of the fastener on-line. Therefore it is preferable if, in the second method the polymer particles are thermoplastic polymers.

If drops of liquids are deposited onto a solid release surface and if the surface energy of the release surface is somewhat higher than the surface energy (or surface tension) of the liquid, the liquid will typically perfectly wet the solid, with a contact angle of zero. With liquids, each "solid-liquid" pair has a contact angle, between zero and 180°, with which the liquid drop will, approximately, wet the solid. With semi-liquid, e.g., softened thermoplastic, particles, the process of forming a contact angle is a time-temperature phenomenon. With solid release surfaces of high surface energy a liquid polymer will wet perfectly if given enough time. If this high surface energy release solid surface is kept hot, and a cold solid particle is placed thereon, a process is started in which the contact angle transforms over time, from an initial obtuse angle towards the final zero contact angle. By interrupting this transformation process, e.g., by a suitable cooling, one can achieve any desired contact angle. Therefore high surface energy solid contact release surfaces are useful in the process of the invention. However, the higher the release surface's surface energy, the more difficult it is to finally separate the release surface from the preform projections. Also if the surface energy of the contact release surface is too high in relation to that of the polymer particles there is greater opportunity for unintentional operator error forming a perform projection that is excessively wet to the contact release surface. The danger of overwetting the contact release surface is lower if the surface energy of the contact release surface is not higher than the first surface energy (that of the particle) plus 60 mJ/m$^2$.

High surface energy contact release surfaces also might cause the engaging projection's edge angles being too sharp creating rims that are too thin and which might possibly break off during later use, creating undesired contamination. It is likely sometimes better to accept larger contact or edge angles to provide enhanced security against engaging projections forming with thin weak edges and rims. Therefore it can be preferable if the second method comprises providing a contact release surface whose surface energy is lower than the first surface energy (that of the particle). In this case the edge angle in the product can be determined by material selection rather than by on-line operating parameters. Also the lower the surface energy of the contact release surface, the easier it is to finally detach the perform projections therefrom. However a certain degree of force needed for detaching perform projections from the contact release surface can be beneficial. Some preform projections can be weakly fixed to the front surface of the base. Namely the fixing strength is lower than desired for its intended end use resulting in some engaging projections possibly breaking loose during use. This is a difficult to detect defect. Therefore it is preferable if the contact release surface's surface energy is higher than the first surface energy (that of the particle) minus 23 mJ/m$^2$. With a contact release surface of this level the separation force for detaching perform projections from the contact release surface may be high enough to remove projections weakly fixed to the base front surface thereby providing an on-line fault-detection and correction mechanism.

It is preferable if, in the methods described hereinabove for thermoplastic preform projections (which can also be termed protrusions throughout), the fixing of the front surface of the base with the terminal ends of at least some of the preform projections comprises fixing by heat or fusing.

Fixing by heat can include melting one or the other of the preform projections or the base front surface, depending on the materials and pressure etc. Preferably both the preform projections and the front surface of the base are allowed to potentially melt, and are thereby fused. Fusing is a fixing of the preform projections to the front surface of the base by heat. In this case the preform projections are made up of particles well suited for both sharpening by the release surface, from below, and the covering and fixing to the base by fusing, above. The particles must be liquefied enough to suitably form the contact angle, but must remain solid enough, to permit keeping their edge angles, during the fusing. It is preferred that the thermoplastic polymer particles have a melt flow rate of between 1 and 90 grams per 10 minutes at the conditions appropriate for the selected polymer.

In the subsequent step of the above second embodiment method, the fixing by heat comprises maintaining the contact release surface at a temperature lower than the softening temperature of the polymer particles or preform projections while contacting the front surface of the base with the attachment ends of at least some of the preform projections. The back surface of the base is preferably heated by subjecting it to a heated gas. Furthermore, the gas pressure at the back surface of the heated base is higher than the pressure (e.g. a gas pressure) at the front surface of the heated base, thereby pressing the heated base against the terminal ends of at least some of the preform projections to enhance the fixing thereof to the base. The pressure difference may be enhanced, for example, by applying vacuum from beneath the contact release surface or the front surface of the base.

Also, in this second method embodiment it is not a great problem if the preform projections are of different heights, as long as a sufficiently pliable base, capable of bending down to reach the lower preform projections, is provided. It is especially advantageous if the whole base is thermoplastic and is actually softened, thereby made soft and flexible, easily bending or even stretching when hot.

If desired the base can be fully softened, where fully softening means softening of all components, layers thereof, e.g. in case of a composite, above a softening temperature.

After the separation of the base from the release surface, some preform projections, not fixed to the base, may remain on the contact release surface. These are usually very tiny residual polymer particles which may melt into, and go away with, particles dispersed later. Still by regularly providing for their removal from the contact release surface, the process can be made more uniform and secure. Therefore it is preferable if the method further comprises:

before the dispersing of the multiplicity of polymer particles on the contact release surface;

heating the contact release surface to a temperature higher than the softening temperature of both the polymer particles and the front surface of the base;

contacting the front surface of the base with a heated contact release surface thereby softening the front surface;

suitably pressing the softened front surface against the heated contact release surface thereby fusing the polymer particle contamination residue into the front surface of the base;

providing, for the contact release surface and the base, temperatures suitable for separating the base from the contact release surface;

separating the base from the release surface, thereby cleaning the contact release surface.

This method clearly uses the thermoplastic character of both the particles and the front surface of the base for cleaning the contact release surface. During the steps above, the small amount of residual polymer contamination goes away with, and usually disappears in the front surface of the base. The base can then be utilized as usual. In a continuous operation, e.g. comprising rolls or conveyors, the release surface can be cleaned with every revolution, before each dispersing of particles, thus always keeping the cumulative contact release surface contamination at low levels.

While the preform projections are being fused to the front surface of the base, the base is above the release surface where it is supported by the preform projections and bridges the space between them. If the front surface of the base is above its softening temperature, any molecular orientation therein may cause problems by shrinking at least the bridging portions of the sheet-form base. That can be avoided, for example, with using a composite base with a suitable backing resistant to shrinking. For example a base, comprising a polyester film, or paper, backing and a polyethylene layer coated thereon as front surface, can potentially withstand the shrinking that may occur in of the base. However if shrinkage is a problem it is preferable if the base is free of molecular orientation when fusing the preform projections or particles. Molecularly oriented films cab be pretreated by contacting the front surface of the base with a heated release surface (which could be the contact release surface), thereby rendering the front surface of the base essentially molecularly un-oriented. The tight pressing of the contact release surface to the softened base, during the cleaning step, also can perform this pretreating step as long as the molecular orientation is suitably released.

Heated gas (preferably air) at an elevated pressure can best be provided with gas nozzles ejecting heated gas. The nozzles preferably use electric heating for heating the gas, but the heat source can be any suitable alternative heat source such as gas burners etc. If the base is moved in front of the output orifice of the nozzles so that its back surface is contacted with the ejected hot gas then the base softens. At the same time, the hot gas ejected from the nozzles creates and maintains a gas flow along the back surface of the base, typically parallel to the traveling direction of the base. If the nozzles are fixed and the base is moving in a machine direction, the hot gas flow will have a direction essentially both parallel and opposite to the machine direction. The hot gas flow, e.g. hot air flow, will exert a pulling force on the softened base, dragging the back surface of the base. That will tend to stretch the softened base. The faster the gas flows, the stronger this stretching effect will be. With a low throughput arrangement, i.e., with low hot gas velocities, and especially with a thick base, a base which is essentially free of molecular orientation can be used. In case of higher throughputs and higher gas flow rates, and especially with a thinner base this machine direction stretching of the base can be very significant, which can be undesirable. For example, stretching of the base in a lengthwise, machine direction can make it difficult to control the thickness of the fastener or can result in rolls of unspecified length. Stretching can also lead to accidental breaking by thinning, tearing apart the base.

The effects of stretching can be counterbalanced by providing a suitable molecular orientation in the base. The problem of stretching can be solved if the base is provided with a heat-shrink potential in the machine direction. The heat of the gas will relax the orientation in the base, i.e., will tend to shrink the base, which will counteract stretching by the heated gas flow. Therefore, in a variation of the second embodiment method, one or more gas nozzles, adapted for ejecting heated gas, are provided. The back surface of the base is contacted with the heated gas ejected by the one or more gas nozzles while the base moves relative to the one or more gas nozzles. The direction in which the base is moving is the machine direction and is essentially within the plane of the base. The base preferably has a heat-shrinkability in the machine direction (the lengthwise heat shrinkability) of at least 1 percent. The fixing by heat includes heating the base above a heat shrink temperature thereof.

As used herein, "heat-shrinkability" in a direction shall mean, in the context of a material such as the base material, that the material is capable of being decreased in its length in the given direction, or dimension, in response to the transmission of thermal energy into the material. The "heat shrinkability" of the material is a percent value and equals 100 percent times the difference between its pre-shrink length and post-shrink length, divided by its preshrink length, in the given direction. The post-shrink length, in a given direction, of the material means the length of the material, in the given direction, after shrinking the material, such as at a temperature of 170° C. for 45 seconds. Shrinking can be determined, for example, by immersing the material into hot silicon oil and letting it freely shrink. It was found that using temperature of 140° C. for 14 seconds relaxes essentially all the shrink in usual polymer materials. As used herein, the "shrinking temperature" of a material refers to the temperature at which the material, exposed to an increasing temperature, starts to heat-shrink.

The advantage of this variation of the second method of the invention is that it helps counteract stretching effects exerted on a softened base by ejected hot gas flow. With high production rates lengthwise heat-shrinkability higher than 1 percent can provide improved results. Therefore it is preferable if, in this variation of the second method, a base having a lengthwise heat-shrinkability of at least 10 percent, more preferably at least 20 percent, more preferably at least 30 percent, even more preferably at least 40 percent, and even more preferably at least 50 percent is provided for the contacting and the fixing depending on the forces created by the hot gas flow and the production rate.

The stretching effect, exerted on the base by a lateral hot gas flow is less significant, or even close to zero (depending on the details of the nozzle arrangement) in the crosswise direction, i.e., in the direction perpendicular to the direction of the traveling path of the base (in a machine it is called the cross machine direction). Therefore, if a base has a high heat-shrink potential, or high heat-shrinkability in the crosswise direction, the edges of the base can shrink or neck in, which results in folding or wrinkling when contacted with the hot gas. This is undesirable. Therefore it is preferable if the heat-shrinkability, of the base in its in-plane direction perpendicular to the main or machine direction is either zero, or lower than the lengthwise heat-shrinkability. "Zero crosswise heat-shrinkability", as used herein, includes the case in which the base exhibits an increase in length, or stretch, rather than shrinking, in the crosswise direction when exposed to heat. The advantage of this difference in heat shrinkability is that it provides a differentiated counteraction to the differentiated dragging effects of the hot gas flow on the softened base in the two orthogonal dimensions. Generally the heat-shrinkability, of the base in its in-plane direction perpendicular to the main direction (the crosswise direction) is lower than 50 percent. Preferably, the crosswise heat-shrinkability is lower than 40 percent, more preferably lower than 30 percent, even more preferably lower than 25 percent, depending on the forces created by the hot gas flow and the production rate. On the other hand, the base heated by the hot gas will exhibit a crosswise thermal expansion which may cause wrinkles in the product. That can be counterbalanced with a suitably low, but positive level of heat-shrinkability provided in the base in the crosswise direction. Therefore it is preferable, if, in the aforementioned situation, the crosswise heat-shrinkability of the base is at least 1 percent.

As discussed above, the dragging or stretching effect in the length direction from the gas nozzles is counteracted by a lengthwise heat-shrinking, which together will generally define a final length of the formed fastener product as related to the initial length of the provided base. If the lengthwise heat-shrinkability of the base is relatively low and the gas nozzles eject a strong hot gas flow, the fastener product will be longer than the initial base material from which it was produced. By increasing the heat-shrink potential and perhaps decreasing the gas pressure or gas flow of the nozzles, the trend of elongated fasteners can be reversed, and the formed fastener can be shorter than the base from which it was made.

The second method of the invention also includes the step of dispersing the polymer particles on the contact release surface so as to form separate preform projections. Preferably it should be avoided that many or most particles, which will form the preform projections, touch adjacent particles, or preform projections, before the preform projections are completed and solidified. Premature particle contact results in a unifying of the neighboring particles or preform projections. However if in a fastener the engaging projections are close to each other, the fixing strength of the fastener is generally higher, i.e., the fastener performs better. As in this method the dispersing, e.g., scattering, of the particles is typically implemented as a stochastic process, the closeness of the projections usually does not reach the theoretically possible maximum value, i.e., the projections could even be a bit closer to each other in the end product. After the fastener is completed, a subsequent moderate heat shrinking thereof can improve the relative closeness of the fastener engaging projections if desired. However, in order to perform this step the base of the formed fastener must have some heat-shrinkability. Therefore it is advantageous if, in this variation of the second method of the invention, the formed fastener base, has a residual lengthwise heat-shrinkability of at least 1 percent. Preferably, a formed fastener, has a lengthwise heat-shrinkability of at least 5 percent, more preferably at least 10 percent, more preferably at least 15 percent, even more preferably at least 20 percent, even more preferably at least 25 percent in this embodiment. In this method the formed fastener is subsequently heat-shrunk at least in the main direction. This heat-shrinking can be by any suitable way of transmission of thermal energy into the formed fastener but preferably in a way such that the acute contact angles, and the geometric features of the engaging projections in general, are kept essentially intact or are at least suitably protected. Preferably the heat energy is transmitted into the formed fastener from the back surface of the base of the fastener. For example this could be done by depositing hot material, e.g., hot melt adhesive, onto the back surface of the base as part of a fixing of the fastener to a substrate. The heat-shrinking should be kept at a low enough level so as to keep adjacent engaging projections separate from each other sufficient for the engaging fibres of a female fastener part to penetrate between adjacent engaging projections. Preferably the fastener base is heat-shrunk by about 0.1 to 25 percent or less.

Economical base materials, e.g., blown or cast thermoplastic polymer films, may not be readily or economically available with the appropriate heat shrink parameters, as these films often have higher heat-shrinkability values than are required. A suitable base can be produced from these economical base materials with a pre-treating step. The pre-treating suitably decreases the heat-shrinkability of the materially in a controlled, partial relaxing of its molecular orientation without letting it shrink entirely. Namely, if a high heat shrinkable film is mechanically kept from freely shrinking and is simultaneously kept hot or softened, its heat-shrinking potential or heat-shrinking capability will gradually decrease with time without the material actually decreasing in length or area to the corresponding extent. Therefore it is preferable if these types of base materials are pre-treated prior to contacting and fixing of the base material front surface with preform projections. The pre-treating of the base comprises providing a pre-treating release surface;

heating the pre-treating release surface to a suitable temperature higher than the softening temperature of the front surface of the base;

contacting and pressing the front surface of the base with the pre-treating release surface thereby softening the front surface;

keeping the softened front surface in contact with the heated pre-treating release surface while preventing the base from shrinking freely, for a suitable period of time thereby decreasing at least its lengthwise heat-shrinkability;

providing, in the pre-treating release surface and in the base, temperatures suitable for separating the base from the pre-treating release surface; and separating the base from the pre-treating release surface.

The release surface used for the pre-treating, i.e., the pre-treating release surface can be similar to or different from the contact release surface discussed above. The pre-treating release surface must be able to suitably release the base at the right time. The base preferably is essentially prevented from any shrinking, e.g. in order to maintain its regular dimensions, but mainly its length. This could be done by keeping the base front surface in full contact with the pre-treating release surface. For that purpose, the tack between the softened front surface of the base and the pre-treating release surface (e.g., a polytetrafluoroethylene surface) can be exploited. In order to do this residual air between the two surfaces should preferably be removed while contacting and pressing the base to the pre-treating release surface. The lengthwise heat-shrinkability of the base is decreased to a suitable value while he crosswise heat-shrinkability rate may (and preferably will) also be decreased. The longer the contact time and higher the temperature, the more the decrease in the heat-shrinkability will be, and vice-versa.

It may be desirable if the length of the base at the start the process is not too much different from, or equivalent to, the length of the fastener product made therefrom, at the end of the process. As it was seen, this can be influenced by setting the right lengthwise heat-shrinkability in the pre-treated base. Therefore it is possible that in the pre-treating process a decreased value of lengthwise heat-shrinkability is achieved such that the pre-treated base length is essentially the same as the formed fastener length. Within this method step if the balance decreased value can be continuously maintained by regulating, during the pre-treating of the base, one or both of;

the temperature of the pre-treating release surface, and the duration of the base contact with the pre-treating release surface.

A practicable manufacturing arrangement using a pre-treating step is using an endless release belt with a release outer belt surface kept in a circulating motion along a belt path; and for pre-treating the base a first portion of the outer belt surface, being at a first location of the belt path, is used as the pre-treating release surface; and for forming the fastener from the pre-treated base a second portion of the outer belt surface, being at a second location of the belt path suitably displaced from the first location, is used as the contact release surface; and the base is provided in the form of a continuous base film kept in a motion synchronous with the belt, and is contacted with the outer belt surface at the first and second locations.

This solution is advantageous because a single release belt is used for pre-treating the base and further producing the fastener from the pre-treated base, which can provide for a zero length-difference between the initial base and the final product. This zero length-difference is desired to conveniently use the same belt, running in all of its points with the same speed, for two different purposes, i.e., for pre-treating the base on the one hand and for depositing the particles to form preform projections and contacting and fixing the pre-treated base therewith on the other hand. The release surface speed at the first location is desirably the same speed as the initial base speed and the release surface speed at the second location is desirably the same speed of the final formed fastener product. If the decreased value of lengthwise heat-shrinkability of the base provided by the pre-treating deviates from a balance value, this section of the base will tend to either get shorter or longer. That can be detected with providing a base film buffer with dancing roller(s) and detecting the trend of motion of the dancing roller(s). If the free section of the base film between the two belt locations should shorten then the lengthwise heat-shrinkability of the pre-treated base could be decreased and vice versa. The lengthwise heat-shrinkability of the pre-treated base can be decreased more by elevating the temperature of the belt at the first location and/or lengthening the first portion of the outer belt surface along which the belt and the base are in contact thereby lengthening the duration of the pre-treating of the base, and vice-versa. This solution has an additional advantage that the outer release belt surface is cleaned from any potential polymer particle contamination by contacting the softened thermoplastic front surface of the pre-treated base with the release belt with every revolution of the belt.

It is further the object of the present invention to provide a new fastener product, readily achievable through the methods above, having corresponding advantages.

The product of the invention is a fastener for engaging with a loop fabric, a sheet-form base having a front surface with a multiplicity of solid and preferably essentially solid or rigid engaging projections. The engaging projections have a top end and an attached end (which can also be termed throughout as a foot). The attached end is joined to the base front surface at a fixing portion. In that there is a fixing of the engaging projections to the front surface of the base, the base and the engaging projection can be formed of different materials or the same materials. The at least one engaging projection projecting from the base front surface can be formed to have an essentially flat top by a deforming surface in the first embodiment method or by the contact release surface in the second embodiment method. However, generally the top end has been subject to a deformation treatment such that it has a different form than the attached end of the engaging projection. If the deformation surface and or the contact release surface are flat then the top end will be correspondingly flat as formed. The top will also generally overhang the base at least partly, where the overhanging portion is also referred to as rim.

The top of the engaging projection as formed will also have a definite edge bordering the top. The engaging projection will also have a mantle surface, meeting the top along the edge, extending from the edge of the top to the attached end of the engaging projection at the front surface of the base. The mantle surface and the top surface close to form acute edge angles generally along the entire edge.

During use, the engaging projections should essentially behave as solid bodies fixed to a base, which preferably is flexible. The meanings of "flat top" and "side view" were discussed earlier herein and are visualized, for example, in FIGS. 3, 4 and 5. As used herein, a strictly convex contour line of an engaging projection, in a side view is convex when looking from the outside and not straight. A strictly convex shape for the lower surface of the overhanging rim or mantle surface has been found to be beneficial because it gives a relatively large thickness to the at least one engaging projection. In at least one side view of the at least one engaging projection, the mantle surface is preferably strictly convex at least at a part thereof adjacent to the edge. This convex shape provides strength to the edge of the rim overhanging the base. A convex shape also effectively leads engaging fibres down towards the base, thereby reducing torque load on the engaging projections and the base where they are attached, as was discussed above. In a different preferred embodiment the engaging projection is strictly tapered from the top to the front surface of the base in at least one side view of the at least one engaging projection The invention fastener has desired advantages. It can provide good shear strength engagement with low loft loop fabrics, including ultra thin nonwoven fabrics. It can also provide shear strength in all directions and is therefore essentially isotropic. The invention fastener can also be manufactured with dense and small projections with generally flat tops and a flexible base making it skin-friendly. There is great flexibility in selecting the base relative to the particles forming the engaging projections. The invention fastener can also be low cost.

Preferred forms of the product, some of them corresponding to the preferable embodiments of the methods described above, can offer various advantages.

First it is advantageous if the fastener at least one engaging projection, in at least one side view of the mantle surface is strictly convex at least in all portions adjacent to the side edge.

Further, it is advantageous, if the fastener at least one engaging projection in each side view of the mantle surface is strictly convex at least in all portions adjacent to the side edge. It is also advantageous if the fastener at least one engaging projection, in each side view strictly tapers from the top to the front surface of the base. The mantle surface and the top surface of the engaging projections define edge angles. These edge angles are advantageously along the entirety of the edge and have an angle of between 15° to 85° or between 30° and 80°. It is further advantageous if the fastener at least one engaging projection, is strictly convex in at least one side view of the entire mantle surface. This effectively leads the engaging fibres down to the front surface of the base, to reduce torque load. It is further advantageous if the fastener comprises at least one engaging projection which is strictly convex in each side view of the entire mantle surface.

The fastener advantageously also includes some engaging projections which are constituted by at least two polymer granules unified with each other, fixed to the front surface of the base.

It is also advantageous if, the material of the front surface of the base differs from the material of at least one engaging projections mantle surface where they are attached. It is even more advantageous if the material of the front surface of the base is softer than the material of the mantle surface of the at least one engaging projection as determined, for example, by differing Shore hardness values.

It is also advantageous for some uses if the fastener base is elastically extensible within a plane of the base, and the material of the mantle surface of the at least one engaging projection is non elastomeric. The base can comprise elastomer materials including elastic laminates or the like. This can make an elastic fastener product, which can be especially beneficial, for example, with diapers and wrapping tapes.

In addition, the invention fastener can also be used in other fields, such as in self adhesive fastener tapes for fixing carpets or polymer sheets to floors or tiles and fabrics to walls of a room.

The invention fastener can also be formed on the surface of a variety of base materials. This could be a film as described above but could be any suitable surface such as a fabric, nonwoven, metal sheet or foil, molded plastic, paper, breathable film, laminate etc, as described above for the first method. For example, engaging projections could be formed on a water insulating membrane used for insulating flat roofs of buildings against rain. This membrane could then be fixed on top of a nonwoven felt on the roof. This system would provide water insulation in combination with a beneficial, lateral vapour migration in the felt, under the insulating membrane.

As it has been said, it is a further object of the present invention to provide improved disposable diapers using the invention fastener.

In this aspect, a disposable diaper comprises:
a bodyside surface;
an opposite, outer surface, comprising a nonwoven fabric;
at least one male fastening component of the present invention for fixing the diaper about a wearer;
at least one female fastening component, comprising fabric, for separably engaging with the at least one male fastening component during the fixing. The female fastening component may be formed by the nonwoven fabric on the outer surface of the diaper. The separable engagement between the at least a portion of the nonwoven fabric of the outer surface of the diaper and the at least one male fastening component of the invention preferably has a shear strength of at least 4.9N.

The term "diaper", as used herein, also includes infant training pants, incontinence garments and the like. The said portion of the nonwoven fabric of the outer surface can be a strengthened portion where, the fibres of the nonwoven of the outer surface take part in engaging with the male fastening component. The said portion can be strengthened, for example, by providing a sufficiently stiff film layer under the nonwoven or by impregnating the nonwoven of the outer surface etc. The term "shear strength" refers to a peak shear strength or force achieved during a shear separation of the male fastener from the female fastener component. An appropriate selection of the nonwoven on the outer surface of the diaper and the male fastener component of the present invention will result in the fastener being capable of engaging with the nonwoven outer shell of the diaper strongly enough to securely keep the soiled diaper in a folded state without a separately provided loop. With a suitable selection of a nonwoven on the outer surface of the diaper, the fastener can be attachable to any suitable point of the diaper outer shell and the attachment of fixing is comfortable and secure. Preferably, the whole of the nonwoven of the outer surface is such a suitable nonwoven.

To make it even more secure, it is preferable if, in the diaper, the separable engagement, between the engagable portion of the nonwoven fabric of the outer surface and the at least one male fastening component of the invention, has a shear strength of at least 9.8 N.

In an even more preferable diaper, the at least one female fastening component is constituted by at least a portion of the nonwoven fabric of the outer surface.

Such a selection of the nonwoven of the outer surface of the diaper, and the suitable kind of fastener makes using of a separate frontal tape comprising a special loop fabric in the landing zone unnecessary. This provides considerable cost saving. It just needs a suitable surface area selected for the fastener to achieve a desired fixing strength for securing the diaper around a wearer during use.

It is even more preferable, if in the latter diaper, the separable engagement between at least a portion of the nonwoven fabric of the outer surface of the diaper and the at least one invention male fastening component has a shear strength of at least 2.5 N/cm$^2$. Here the necessary shear strength is specified as a shear strength specific of 1 cm$^2$ unit area of contact surface between the nonwoven and the fastener.

To make it even more secure, it is further preferable if, in the diaper, the separable engagement, between at least a portion of the nonwoven fabric of the outer surface and the at least one male fastening component, has a shear strength of at least 3.5 N/cm$^2$.

It is a further object of the present invention to provide an improved wrapping tape. Such wrapping tape has a first side with an exposed textile or nonwoven material, and an opposite second side, comprising a male fastening component of the present invention suitable for engaging with the textile or nonwoven material for fixing the wrapping tape around an object. The textile or nonwoven material also includes low loft fabrics with some free fibres capable of mechanically engaging with the male fastener materials of the present invention. The advantages of this wrapping tape are that it has fine touch, is easy to write upon with ink, can be flexible, extensible or stretchable, is inexpensive, and is novel in its appearance. With a porous, e.g., micro-perforated or nonwoven, base and a suitable nonwoven loop textile, this wrapping tape even be used as house wrap.

BRIEF DESCRIPTION OF THE DRAWINGS

FIG. 1a is a schematic side view of the apparatus for manufacturing a fastener of the invention.

FIG. 1b is a magnified view of a portion of FIG. 1a, including the side view of a preform projection.

FIG. 3b is a top view of the engaging projection of FIG. 3a.

FIG. 3c is a side view of the engaging projection of FIG. 3a.

FIG. 4a is a perspective view of an engaging projection, a "merged projection".

FIG. 4b is a top view of the engaging projection of FIG. 4a.

FIG. 4c is a side view of the engaging projection of FIG. 4a.

FIG. 5a is a perspective view of a multi-story engaging projection.

FIG. 5b is a top view of the engaging projection of FIG. 5a.

FIG. 5c is a side view of the engaging projection of FIG. 5a.

DESCRIPTION OF THE PREFERRED EMBODIMENTS

Example 1

Method for Forming a Fastener

Figure 2:
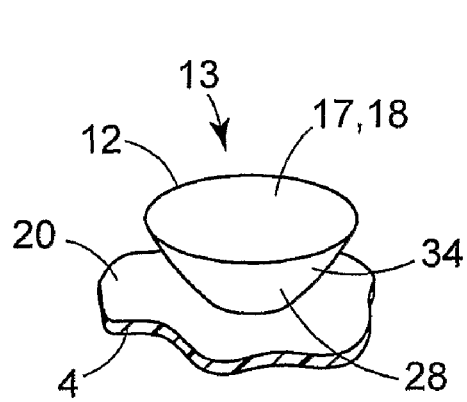
FIG. 2 is a top view of a fastener.
Figure 3B:
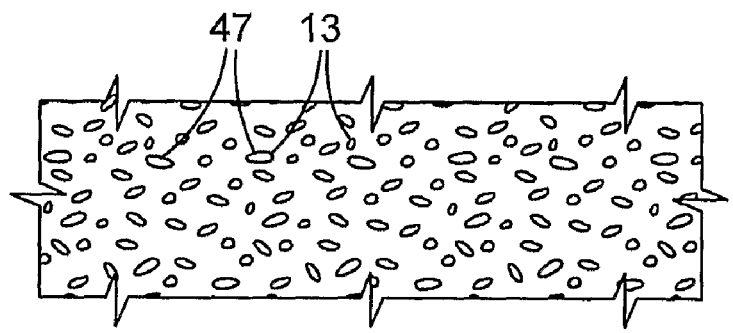
Figure 3A:
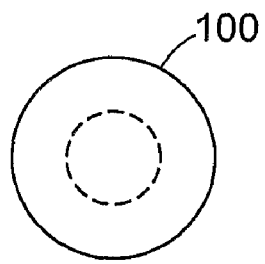
FIG. 3a is a perspective view of an engaging projection.
Figure 3C:
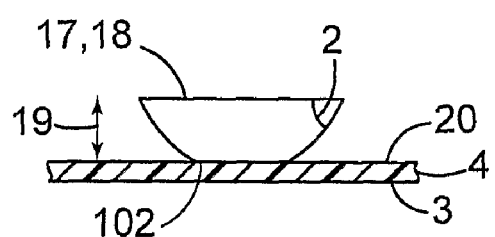
Figure 6:
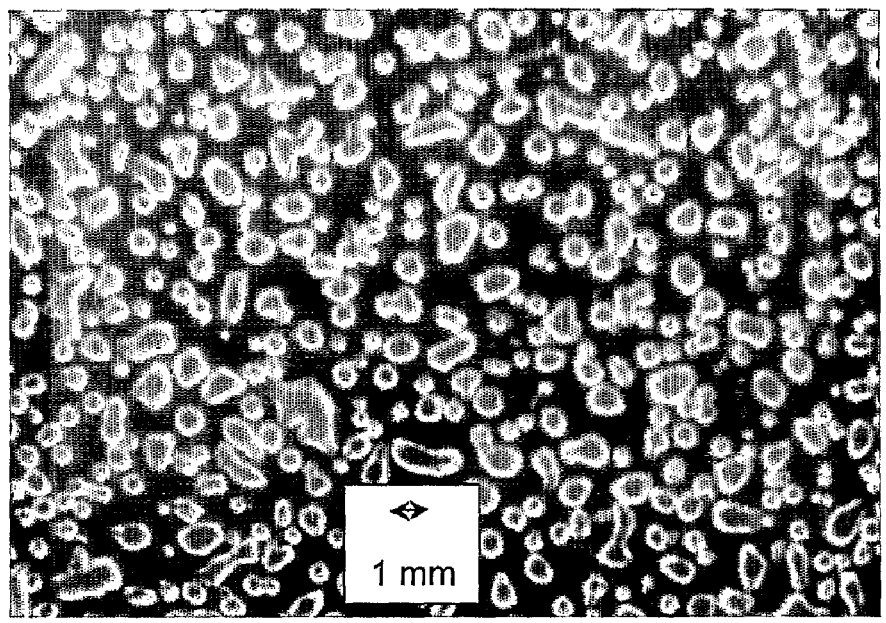
FIG. 6 is a photographic picture, a top view of a fastener.
Figure 7:
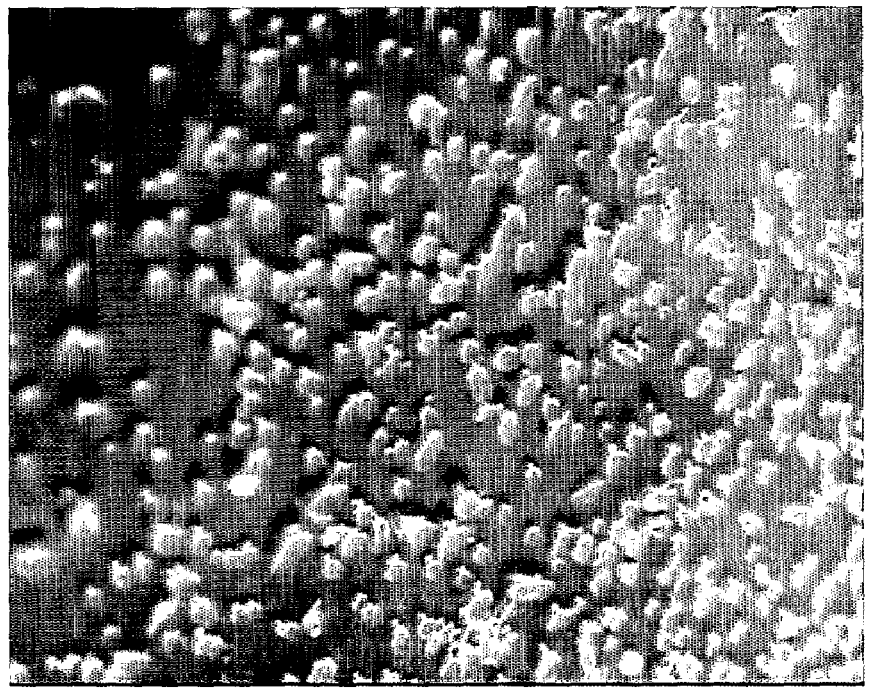
FIG. 7 is a photographic picture, a perspective view of a fastener.

Reference is made to the method depicted in FIG. 1a. Using the second embodiment method, of the invention, high density polyethylene powder granules, Du Pont Polymer Powders of Switzerland S.A. ND 5374-F (described as made by size reduction and screening from a reactor powder), are provided, as polymer particles 36. These powder granules had a nominal maximum size of 150 microns, with a majority of the particles being between 80 and 110 microns; a melting point of 130° C.; melt flow rate of 20 grams per 10 minutes. The surface energy of the polymer is about 31 mJ/m$^2$. A base 4 of a 80 micron thick monolayer polyethylene film sheet was used, the sheet being of a mixture of low density polyethylene (80 percent by weight, FA 2210, 0.26-0.35 melt flow rate (2.16 kg/190° C.) by TVK rt Hungary) and linear medium density polyethylene (20 percent by weight, FS 340-03 by TVK rt Hungary). The contact release surface 40, which could be on a release conveyor 39, was a "Chemglas 100-6" brand brown PTFE-coated glass fibre web, with a slightly textured surface, from Lörincz kft of Hungary. PTFE stands for polytetrafluoroethylene. The surface energy of the contact release surface 40 was 18.5 mJ/m$^2$. A release conveyor 39 if used would be driven around two drive rollers 11. The contact release surface 40 was kept horizontal.

At the beginning of the operation cycle, the horizontal contact release surface 40 was kept at a temperature of about 170° C. by a hot plate 24. This could be done under the release conveyor 39, though further hot chambers, on the top side of a release conveyor, could also be utilized. A scatter unit 42 (generally a hopper with a feeding wheel and an underlying screen) was used to evenly disperse the polymer particles 36 on the heated contact release surface 40, at an average density of about 500 granules per cm$^2$, corresponding to about 15.7 g/m$^2$. As distributed on the contact release surface it appeared that almost every particle stayed separate from the others forming separate preform projections 37 sitting on and projecting from the release surface 40 to corresponding terminal ends 46. The particles were heated by the heat of the release surface 40, and thereby kept softened or melted, i.e., in a semiliquid state. About 20 seconds after the particles where distributed on the release surface 40, they formed preform projections 37 having acute contact angles 7, along their edges 12 contacting the release surface 40. which were about 59° on average as measured by photograph. Thus 20 seconds after the particles were distributed on the contact release surface 40, the preform projections 37 form acute contact angles. During this time, almost every particle remained alone (as shown in FIG. 2), however, some of them melted together with their neighbors, forming "merged preform projections" 47, as shown in FIG. 2. Then the release surface 40 was then cooled down to, and kept at, a temperature of about 65° C., which could be done by an air blower 1. Cooling is important for later preserving the contact angle of the preform projections 37, and was provided by a steel plate 45 at a controlled temperature under the contact release surface 40. Thereby the preform projections 44 were made solid and suitable for contacting with the front surface 20 of the base 4. The base 4 was laid over the preform projections 37 on the contact release surface 40. The front surface 20 of the base 4 contacted the terminal ends 46 of the preform projections 37, i.e., the tops of the, semi-lenticular, solidified droplets. A hot air blowing unit 23 was fixed, about 15 mm above the back surface 3 of the base 4. As hot gas 21, air of 650° C. (the setting of the heater) was blown on the back surface 3 of the base 4, which could be done while the release conveyor 39 and the base 4 are together kept in motion in a lateral direction 25. As calculated from the force of the air the blowing air produced an over-pressure of about 386 Pa at the back side of the base 4. Each point of the base 4 was calculated as exposed to the hot air for about 0.26 seconds (using a line speed of 2.3 m/min). That was enough for the base 4 to soften enough to be pressed onto, and fixed with, the terminal ends 46 of the preform projections 37. The terminal ends 46 also melted from the heat, to a suitable extent to fuse the preform projections to the base. The free heights 19 of the preform projections were preserved as were the contact angles 7 as the edge angles 2. Then everything was cooled which could be done by air blower 1, whereby the base 4 regains a flat shape. The base 4, together with the engaging projections 13 fixed thereto, was separated and removed from the contact release surface 40, which could then wound up in a reel 38 using the method of FIG. 1a. The engaging projections 13 formed had flattened tops 18, with a rim 100 overhanging the base 4 typically in all directions, and bordered, typically all around, by an edge 12 whose angle 2 essentially corresponds to the contact angle 7, which edge angle was about 59° on average in this example. The vast majority of the engaging projections 13 strictly taper (strictly convex), in each side view thereof, from the flattened top 18 to the attached end 102 at the front surface 20 of the base 4.

If using the method of FIG. 1a the cooled portion 9 of the release surface 40 after removing the preform projections 37, could then be turned back for the next operation cycle. However, before the next dispersing of particles onto the contact release surface, the contact release surface 40 should be cleaned as follows. The contact release surface 40 can be heated to 170° C. with a heating means 22. An essentially biaxially molecularly oriented polyethylene film 35 with front surface 29, serving as the base 4, is provided. The molecularly oriented base 4, can be contacted and pressed to the heated release surface 40 with a silicone rubber roll 41. The base 4 is softened and pressed into the fine texture of the surface of the contact release surface. This prevents the base 4 from shrinking while its molecular orientation decreases. Also, the pressing causes contamination 8 of residues of polymer particles 36, possibly left on the release surface 40 from the preceding operation cycle, to fuse into, and disappear into the front surface 20 of the base 4. Then both layers are cooled down with air blower 1 and the base 4 separated from the cleaned release surface 6, both ready for the next operation cycle.

The example was actually done on a lab line that simulated the conditions of the apparatus of FIG. 1, the difference being that a continuous belt was not used but rather a platform having the heating plate and the contact release surface was driven by a speed controlled carriage. This carriage was driven under a scattering unit and hot air blowing unit as described above.

Example 2

A Method for Forming a Fastener

Reference is made to the method depicted in FIG. 1a. This method slightly differed from that of the Example 1 in that a release surface 40 of polyester film was provided having a surface energy of about 52 mJ/m$^2$. The contact release surface was at a temperature about 150° C. The contact time in this example about 30 seconds, at which time the contact angles 7 formed were observed to be about 43° on average.

Example 3

A method for Forming a Fastener

This method slightly differs from that of Example 1 in that the base 4 was a polyester film coated with a polyethylene layer, the latter being used as the front surface 20. At the start, the film had molecular orientation in the polyethylene surface 20. The contact release surface was first cleaned by polyethylene face of the polyester film. During the whole process cycle, the polyester was kept at a temperature lower than its shrinking or softening temperatures.

Example 4

A Method for Forming a Fastener

Using the second embodiment method, of the invention droplets of a UV-Lacquer, i.e., of a lacquer crosslinking by UV, i.e., ultraviolet, irradiation, were provided as particles to form preform projections using the contact release surface in Example 1. With a lacquer called "Sollux D 1770 GL 0610" from Herberts Mobellacke GmbH, in about 10 seconds uniform contact angles were observed of about 40° formed all around the edges of the preform projections.

A suitable viscosity could be set to about 40 to 75 seconds at 20° C. with a thinner, measured with DIN CUP 4. The lacquer could be uniformly dispersed with nozzles or spray heads, in the form of droplets of about 200 microns, over the contact release surface. The contact angles are formed without heating. (UV-lacquers of lower odour are available with similar surface energy, though at higher prices.). By a subsequent UV irradiation they can be hardened. The base could be a fully thermoplastic film, with zero molecular orientation, with a coextruded front surface of any suitable, e.g. acrylic-based, hot adhesive co-polymer or tie layer material. The base would be laid over the release surface with the preform projections; hot gas could be used to soften the base from its back surface, and the base pressed against the cured preform projections and then cooled, thereby providing a suitable fixing with the preform projections. After cooling, the base could be removed, separating the newly formed, engaging projections from the release surface.

Example 5

A Method for Forming a Fastener

Reference is made to FIGS. 5a-5c. Using the second embodiment method, of the invention a base of a polyethylene film as used in example 1. This example differed from example 1 in that the polyethylene film was pre-roughened in its front surface with granules. The pre-roughening granules were fixed to the base front surface. The pre-roughened front surface was prepared by keeping the base at about 170° C., bringing to its front surface cold granules (Solvay "Eltex"—a high density polyethylene, of 315-500 microns in size, of a polymer of a density of 0.938 and of a melt flow rate of 2.6) at about 160 granules per cm$^2$. During this method, especially during the fixing of the front surface with granules the pre-roughening projections are kept from being deformed too much. The preform projections are fixed to the tips of the pre-roughening granules, thus forming multi-story engaging projections 31 as shown in FIGS. 5a-5c, which are capable of engaging with thicker loop fabrics.

Example 6

A Method for Forming a Fastener

Using the first embodiment method, of the invention, a polyethylene film, identical with that of Example 1, is provided as sheet-form base. High density polyethylene powder granules (Du Pont Polymer Powders of Switzerland S.A. NY 6454-F, made with size reduction and/or screening from a reactor powder). These powder granules had a nominal maximum size of 200 microns, the majority of the particles being between 90 and 140 microns, a melting point: 131° C. and a melt flow rate of 8 grams per 10 minutes. The surface energy of the polymer of the particles is about 31 mJ/m$^2$. The base was kept at a temperature of about 170° C. and the particles were randomly dispersed onto the heated base with a scatter unit, and after a suitable time the roughened base was cooled, the time being long enough for a strong fixing of the particles and short enough to keep a definitely undercut shape of the projections, in which their attached ends were smaller than their top view. The projections are thus made up by the particles, typically containing one particle each. A nip, which could be a PTFE conveyor, was used as the contact deformation surface. The base was cooled by contact with a metal cooling surface from its back surface, keeping the attached end of the projections solid, while the terminal ends of the projections on its front surface are contacted with, and heated to melt by, the contact deformation surface as they pass through the nip. The PTFE conveyor was kept at a temperature of about 160° C. The compression of the nip, and the line speed, are set in a way in which the deformed projections are flattened, their flat tops had a rim overhanging the base outside the attached end in all directions.

During this process the contact can take about 0.2 to 10 seconds, depending on the nip parameters after which the deformed projections surface is cooled and the nip opened. Thereby the formed flat top surfaces are bordered by edges whose angle is essentially determined by the acute contact angle. By the facts, that the projections are, at the start, definitely undercut, i.e., narrow near the front surface of the base, and that their top portions are flattened, the engaging projections are typically provided with a shape in which, in each side view thereof, the engaging projection strictly tapers from the flat top surface to the front surface of the base. The particles are, at the beginning, scattered with a suitable closeness in order that during the deforming of the heated terminal ends of the projections, some engaging projections can be unified with other, neighboring, engaging projections, i.e., they melt together at an interface, forming a somewhat elongated engaging projection.

Example 7

A Fastener. Reference is Made to the Figures

The fastener 14 in this example was that made in Example 1. It is a fastener 14 suitable for engaging with a thin or ultra thin, e.g. nonwoven, loop fabric, in a diaper 10. The majority of the engaging projections 13 of the fastener 14 were constituted by exactly one polymer granule with some "merged projections" 47, constituted by at least two polymer granules, unified with each other. The engaging projections 13 comprises a edge 12, being in the plane of a flat top 17 bordering the flat top 17. Mantle surface 28, met the flat top 17 along the edge 12, extending from the edge 12 to the attached end 102 at the front surface 20 of the base 4. The mantle surface 27 and the flat top 17 close acute edge angles 2 of about 59° on average in this example, along the entirety of the edge 12. The edge angle 2 was essentially determined by the acute contact angle 7 during the formation of the top surface 17. In all side views of each engaging projection 13, the whole mantle surface 28 was strictly convex, preserving the lenticular, rounded drop-shape of the preform projections 37, used in the manufacturing process. Further each engaging projection 13, typically in all side views thereof, strictly tapered from the flat top 17 to the front surface 20 of the base 4. The overall thickness of the fastener 14 was about 140 to 190 microns, with the number of engaging projections 13 being about 460 per cm$^2$. The engaging projections closeness, in combination with their flat tops 17, rendered the fastener 14, extremely smooth to the touch. We have found, that an average adult can hardly, in fact typically not at all, distinguish its front side from its smooth back surface by just touching by hand. Probably due to the relatively small attached end areas of the engaging projections 13, the fastener 14 was perceived to be as flexible as a low density polyethylene film of about 90 to 100 microns.

Example 8

A Fastener. Reference is Made to the Figures

The fastener 14 in this example was different from that in Example 7, in that this fastener 14 was made from a thermoplastic elastomer base 4 (a thermoplastic elastomeric film obtained from Tredegar CEX-802 WR, 54 g/m$^2$), the film appeared to be coextruded. This elastic fastener 14 would be well suited with diapers 10 and wrapping tapes 48.

Example 9

Figure 8:
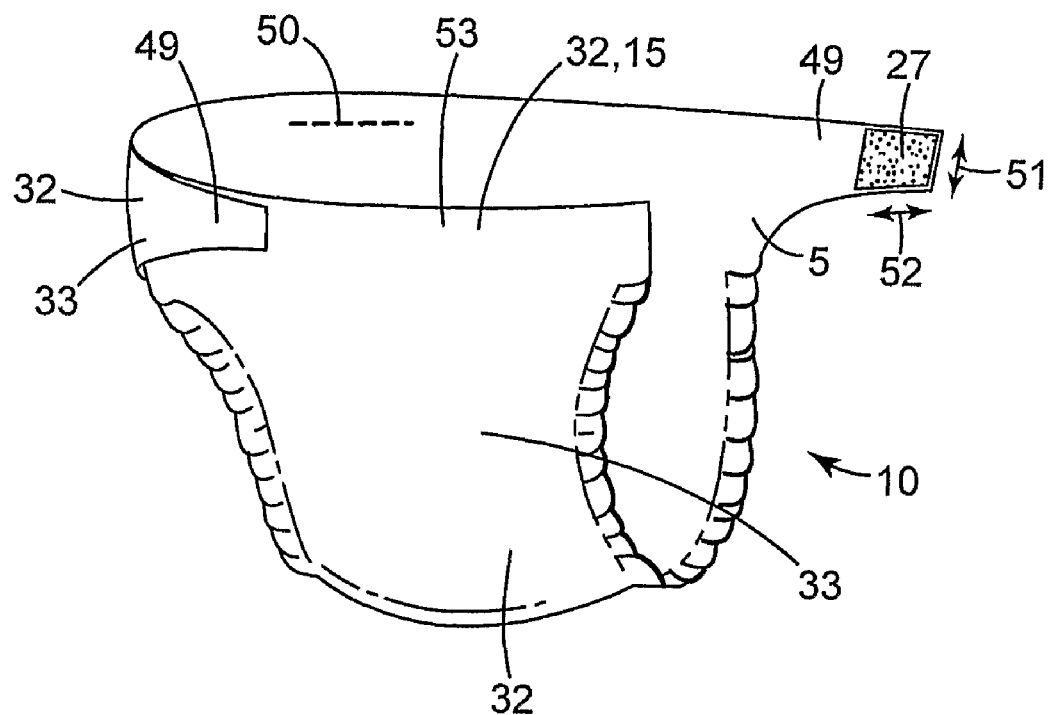
FIG. 8 is a perspective view of a baby diaper.

A Diaper. Reference is Made FIG. 8

The disposable baby diaper 10 comprised a nonwoven bodyside surface 5; an opposite, outer surface 33, comprising a polypropylene spunbond nonwoven fabric 32 of about 20 grams/m$^2$ which is continuously laminated to a breathable polymer film underneath. Its left and right side tapes 49, fixed with their ends to the back portion of the waistline 50 of the diaper 10, comprised two corresponding male fastening components 27, for fixing the diaper 10 about a wearer, at their other loose ends. Each male fastening component 27 was a piece of the fastener 14 of Example 7 the dimensions of each male fastening component 27 were as follows: width 51, in a direction perpendicular to the waistline was 45 mm, length 52 in the direction of pulling, i.e., in the direction of the waistline 50 was 14 mm. The diaper did not comprise a separate loop landing zone 53 for mating with the male fastening components 27. The landing zone was rather formed by the fabric 32 of the outer surface 33 which was capable of creating a separable engagement with the male fastening components 27. The separable engagement, between the nonwoven fabric 32 of the outer surface 33 and each of the male fastening components 27, had a shear strength of about 35 N, corresponding to a specific shear strength of about 5.56 N/cm².

Example 10

Figure 9:
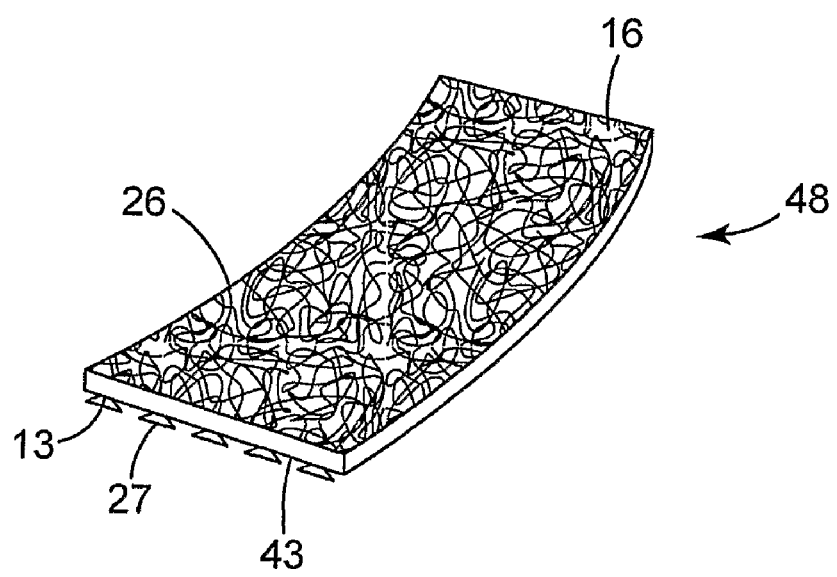
FIG. 9 is a perspective view of a wrapping tape.

A Wrapping Tape. Reference is Made to FIG. 9

The wrapping tape 48 had a first side 16 formed by an exposed spunbond nonwoven loop textile 26 with a base weight of about 14 g/m². The opposite, second side 43 of the wrapping tape 48 comprised a male fastening component 27 suitable for separably engaging with the loop textile 26 for fixing the wrapping tape 48 around an object. The male fastening component 27 of the second side 43 was a fastener 14 according to Example 7.

Example 11

Performance of Male Fasteners of the Present Invention in Comparison to State of the Art Male Fasteners Shear fixing performance, i.e., peak shear strength, of the new mechanical fastener of Example 7 was compared to that of several mechanical fasteners used in commercial diapers, available in Hungary at the end of year 2004. The diapers used were: Huggies Super-Flex (referred to in the following as "H"); Pampers Total Care (referred to in the following as "P"); and Libero Discovery (referred to in the following as "L"), all with dedicated loop frontal tapes in the landing zones, and with nonwoven outer surfaces. The peak shear strength was measured on the commercially available diapers by removing the tape tab and cutting the tab to 20 mm in width and to 14 mm in length in the pulling direction. The loop materials were then adhered to an aluminum panel using a double-sided adhesive tape. Then the corresponding male fastener was pressed in each case onto the loop material by applying finger pressure while simultaneously exerting a shear force of about 0.5 kg in a vertical direction. Then the finger pressure was removed, and the shear load was continuously increased manually by pulling on the laminate with the initial weight of about 0.5 kg being still present until the mechanical fastener separated from the loop material. The load at which the separation occurred was measured as peak shear force and is given in the table below.

Further, the mechanical fastener 27 of the present invention were tested against diaper loop frontal tapes specially designed for use on diapers, hereinafter referred to as follows: "NW": a developmental low-loft spunbond nonwoven diaper loop tape; and "K": a locked loop diaper frontal tape commercially available from Koester, Germany under the trade designation FT-800 T-NC. The frontal tape "K" was commercially available and a state-of-the art diaper loop material used for diapers.

| Female loop component | Male fastener | Peak shear strength (N) |
| --- | --- | --- |
| Frontal tape "K" | Mechanical fastener 27 of Example of the present invention | 37.2 |
| Frontal tape "NW" | Mechanical fastener 27 of Example 1 of the present invention | 30.9 |
| Frontal tape of diaper "H" | Fastener of diaper "H" | 16.7 |
| | Mechanical fastener 27 of Example 1 of the present invention | 16.3 |
| Frontal tape of diaper "P" | Fastener of diaper "P" | 27.8 |
| | Mechanical fastener 27 of Example 1 of the present invention | 17.0 |
| Frontal tape of diaper "L" | Fastener of diaper "L" | Side tape broken at 24.5 |
| | Mechanical fastener 27 of Example 1 of the present invention | 25.0 |
| Nonwoven back of diaper "H" | Fastener of diaper "H" | 6.9 |
| | Mechanical fastener 27 of Example 1 of the present invention | 16.3 |
| Nonwoven back of diaper "P" | Fastener of diaper "P" | 5.9 |
| | Mechanical fastener 27 of Example 1 of the present invention | 17.0 |
| Nonwoven back of diaper "L" | Fastener of diaper "L" | 19.3 |
| | Mechanical fastener 27 of Example 1 of the present invention | 16.7 |

In a separate test long term measurements were made using the following procedure. Test sample strips were prepared with a 100 mm long by 25 mm wide sample of the Example 1 fastener reinforced on the back side with paper (attached with a double-sided adhesive tape) and box sealing tape. This test sample was used to determine the ability of the male fastener of Example 1 to adhere to the loop materials of the commercially available diapers described above. The terminal 14 mm of the fastener materials of the test samples were adhered to the loop materials and nonwoven diaper backs described above by applying uniform finger pressure. A 1.0 kg weight was attached to the opposite end of the sample strips in the vertical direction. All test samples where still hanging after a 24 hour period. Some samples remained attached for well over 24 hours. A mechanical fastener sample made in accordance with example 5 was additionally tested in a long term shear test as described above with frontal loop tape "K" for over 90 days, instead of the above 24 hours.

Example 12

A Method for Forming a Fastener. Reference is Made to the FIG. 10

Using the second embodiment method, of the invention, granules of a high density polyethylene powder, available from Rowak AG under the trade name "Rowalit N-lOO-6 80-200 microns", were provided, as polymer particles 36 These polymer powders had a nominal size range of 80 to 200 microns a melt flow rate of 6 to 8 grams per 10 minutes. The surface energy of the polymer of the particles was about 31 mJ/m². As a sheet form base 4, a monolayer polyethylene film sheet, of 30 microns in thickness, was used, the sheet being a 30 percent to 70 percent mixture (blend) of a first and a second polyethylene. The first polyethylene was a high density bimodal polyethylene available from TVK rt under the trade name Tipelin 8000F and had the following parameters: a melt flow rate of 6 grams per 10 minutes (21.6 kg/190° C.), a density of 0.945-0.951 g/cm³, and Shore D hardness 61. The second grade was a high density polyethylene available from TVK rt under the trade name Tipelin FS 471-02 (2.16 kg/190° C.) and had the following parameters: a melt flow rate of 0.18 grams per 10 minutes, a density of 0.947 g/cm³. The base 4 as initially provided, had a lengthwise heat-shrinkability of about 67 percent and a crosswise heat-shrinkability of about 42 percent. As a release surface 40 a contact release surface, made of the "Chemglas" brand PTFE-coated glass fibre web used in Example 1 except that it was a black antistatic. The actual example was performed on the lab line described in Example 1 above. The contact release surface was heated to at least 140° C., in this example, except the film was pretreated (annealed) on a continuous line such as shown in FIG. 10*a*, as described below.

Figures 10A, 10B:
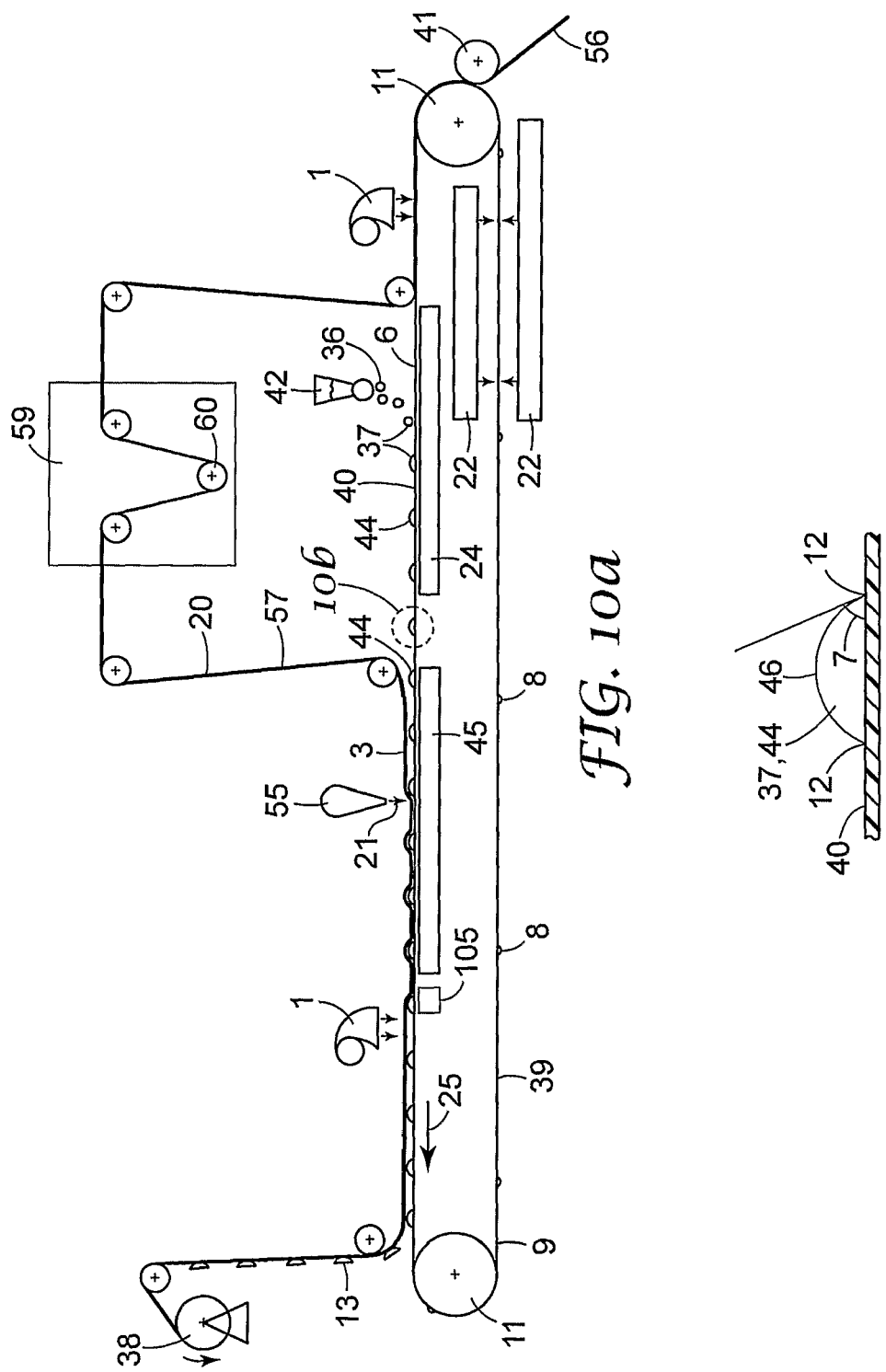
FIG. 10a is a schematic side view of the apparatus for manufacturing a fastener of the invention.
FIG. 10b is a magnified view of a portion of FIG. 10a, including the side view of a preform projection.

This example however could be entirely performed with the continuous apparatus as shown in FIG. 10*a*. In this apparatus a release conveyor 39 driven around two drive rollers 11. The release surface 40 being kept horizontal. At the (preferably heated) drive roller 11 where the upper path of the release conveyor 39 starts (on the right side in FIG. 1*a*), the release surface 40 would be heated with heating means 22. The base 4, at this moment yet being in its molecularly oriented state, was contacted and pressed onto the heated textured release surface 40 (e.g. embossed) with a silicone rubber roll 41 having a Shore A hardness value of 40. The base 4 was, at the moment of contact, softened and pressed into the fine texture of the surface of the Chemglas release surface. This prevents the base 4 from shrinking while it looses some of its molecular orientation. In a continuous process this pretreating could also be used to remove contamination 8, possibly left on the release surface 40 from residues of polymer particles 36 from a preceding operation cycle to fuse into, and disappear in, the front surface 20 of the base 4. The base 4 was in contact with the hot release surface 40 for about 3 seconds. Then the base 4 was cooled down with a air blower 1 and detached from the release surface 40 at a detaching position 54. The pre-treated base 57 had a balance of lengthwise heat-shrinkability of about 51 percent and a crosswise heat-shrinkability of about 19 percent. The film at this point was remove from the continuous line and further treated on the lab line. However using the continuous process the detached pre-treated base 57 could be w lead through a film buffer 59, including a dancing roller 60, positioned above the release conveyor 39, and afterwards lead back onto already formed preform projections 44 on the contact release surface and then moved under the gas nozzle 55. A lengthwise tension of 1.67 grams per cm width was maintained on the pretreated film on the plate in the lab line to keep it smooth. In a continuous process this tension could be maintained by a dancing roller 60 by monitoring the position of the dancing roller 60. If the dancing roller 60 would rise, it means that the base film under nozzle 55 is consumed faster than the pre-treating section feeds the base film into the film buffer 59, i.e., the manufactured fastener is shorter, lengthwise, than the original length of the base 4 from which it is made. This would be caused by the lengthwise heat-shrinkability of the pre-treated base 57 being too high. In this case the detaching position 54 could be displaced, along the release conveyor 39 surface, farther from the drive roller 11 setting the pre treating time of the base 4 higher. Longer pre-treating will relax more orientation which results in a lower residual lengthwise heat-shrinkability in the pre-treated base 57. The regulating process for excessive film being fed into the film buffer 59 is analogously the opposite. This negative feedback could be used to decrease lengthwise heat-shrinkability of the pre-treated base 57 at a balance value in a dynamic feedback control system. Alternatively the temperature of the release surface 40 at the pre-treating section can also be used for dynamically regulating the system to a balance value.

The horizontal release surface 40 could be kept at a temperature of about 100° C. at the place where the polymer particles 36 are scattered. This temperature would be low enough to keep the polymer particles 36 from potentially prematurely softening or melting in the scattering unit 42, but would be high enough to prevent the polymer particles 36 reaching the release surface 40 from bouncing, which is important for uniform dispersing of the polymer particles 36 onto the contact release surface. If the landing area of the contact release surface 40, where the polymer particles 36 first land is not hot enough for at least partly softening the polymer particles 36 the polymer particles 36 will tend to bounce resulting in a non-uniform dispersing. Downstream of the scattering on a continuous line the contact release surface 40 would be heated from underneath to a temperature of about 180° C. The heating on the lab line was provided for by a hot plate 24 underneath the contact release surface 40, which in a continuous process could be under the release conveyor 39, though further hot chambers, on the top side, could also be utilized. The polymer particles 36 on the lab line were evenly dispersed with a scatter unit 42, at an average density of about 340 granules per cm², corresponding to about 16 g/m². The free fall distance of the polymer particles 36 from the scatter unit 42 to the release surface 40 was about 30 mm. A greater free fall of the polymer particles 36 could potentially result in nonuniform dispersing of the particles. Because of the small distance between the hot release surface 40 and the scatter unit 42 the scatter unit 42 was provided with a heat shield below the scattering screen. The heat shield was two cross directionally arranged rows of staggered brass tubes connected to a cooling fluid, which in this case was air, however water or any other suitable cooling fluid could be used. Heat insulators could also be used in other locations where the polymer particles would need to be protected from excessive heating. Almost every particle stayed separate thereby forming separate preform projections 37 on the release surface 40 with corresponding terminal ends 46 also being formed. The particles were heated by the heat of the release surface 40, and thereby transformed into a semiliquid state. About 30 seconds after the polymer particles 36 were placed on the release surface 40, they formed preform projections 37 having contact angles 7 of about 59° in average based on observation by photograph. While on the contact release surface almost every particle remained separate however, some of the particles melted together with their neighbors, forming "merged projections". The release surface 40 was then cooled and maintained at a temperature of about 70° C. That is important for later preserving the edge angle of the preform projections 37, and in a continuous line could be provided for by an aluminum plate 58 of controlled temperature under the release conveyor 39. At this point the preform projections 44 are at least partly solid and suitable for a contacting with the front surface 20 of the base 4. The pre-treated base 57 was laid over the preform projections 37 on the release surface 40. The front surface 20 of the base 4 was in contact with the terminal ends 46 of the preform projections 37, i.e., the tops of the semi-lenticular, solidified droplets. At this moment the pre-treated base 57 had a lengthwise heat-shrinkability of about 51 percent and a crosswise heat-shrinkability of about 19 percent. A hot air nozzle 55 was spaced 10 mm above the back surface 3 of the base 4. The gap of the nozzle 55 is set in the crosswise direction 25 to the motion of the base 4. The gap size was 300 mm in length and 4 mm in width. The hot gas 21 was air at a temperature of 271° C. (measured using a thermocouple near the exit gap of the nozzle) ejected onto the back surface 3 of the base 4 while the base 4 was kept in a motion of a lateral direction 25. The dynamic force of the air stream from the gap of nozzle 55 was measured, 10 mm under the gap, to be 5.89 grams per cm gap length. The speed of the contact release surface was kept at 4 meters/minute. This was enough for the base 4 to be heated over its shrinking temperature and to softened enough to be pressed into, and fixed to the terminal ends 46 of the preform projections 37. The terminal ends 46 also appeared to be partially melted from the heat to a suitable extent to cause fixing with heat, i.e., fusing. The preform projections free heights were preserved as the height of the engaging projections while and contact angles 7 were generally preserved as the edge angles 2. In a continuous process everything could then be cooled down by air blower 1, whereby the base 4 would regain its original flat shape. The base 4, together with the engaging projections 13 fixed was then separated and removed from the release surface 40 and in a continuous process could then be wound up in a reel 38. The engaging projections 13 had flattened tops, with a rim 100 overhanging the base 4 typically in all directions, and continuously bordered by an edge 12 whose edge angle 2 essentially corresponded to the contact angles 7. In a continuous process the cooled portion 9 of the release surface 40 could then be used in the next operation cycle. The fastener made with this process had a lengthwise heat-shrinkability of 47 percent and a crosswise heat-shrinkability of 16 percent. This fastener could be further heat treated to decrease the distance between the engaging projections 13.

Example 13

A Method for Forming a Fastener

This method slightly differs from that of Example 12 in that the nozzle had a gap width of 3 mm, positioned crosswise to the main direction, 10 mm above the back surface of the base. The air ejected by the nozzle was of a temperature of about 600° C. (measured at the nozzle), its dynamic force, measured 10 mm under the gap was 11.77 grams per cm gap length. The base, laid on the tops of the preform projections was pulled with a force of 1.67 grams per cm width to keep it smooth. The temperature of the release surface was 70° C. as it entered under the nozzle. The linear speed of the contact release surface under the nozzle was about 30 meters per minute. The fastener formed was 5 percent longer, in the lengthwise direction, than the piece of base film from which it was made.

Example 14

Performance of Male Fasteners of the Present Invention in Comparison to State of the Art Male Fasteners Shear fixing performance, i.e., peak shear strength, of the new mechanical fastener of Example 13 was compared to that of several mechanical fasteners used in commercial diapers, available in Hungary at the end of year 2004. The diapers used were those described in Example 11 above. The peak shear strength was measured as described in Example 11 above.

Further, the mechanical fastener 27 of Example 13 was tested against the diaper loop frontal tapes designated as "NW" and "K" as was specified in Example 11 above.

| Female loop component | Male fastener | Peak shear strength (N) |
|---|---|---|
| Frontal tape "K" | Mechanical fastener 27 of Example 13 of the present invention | 45.1 |
| frontal tape "NW" | Mechanical fastener 27 of Example 13 of the present invention | 39.5 |
| frontal tape of diaper "H" | fastener of diaper "H" | 16.7 |
|  | Mechanical fastener 27 of Example 13 of the present invention | 26.2 |
| frontal tape of diaper "P" | fastener of diaper "P" | 27.8 |
|  | Mechanical fastener 27 of Example 13 of the present invention | 29.7 |
| frontal tape of diaper "L" | fastener of diaper "L" | side tape broken at 24.5 |
|  | Mechanical fastener 27 of Example 13 of the present invention | 25.9 |
| nonwoven back of diaper "H" | fastener of diaper "H" | 6.9 |
|  | Mechanical fastener 27 of Example 13 of the present invention | 17.6 |
| nonwoven back of diaper "P" | fastener of diaper "P" | 5.9 |
|  | Mechanical fastener 27 of Example 13 of the present invention | 17.7 |
| nonwoven back of diaper "L" | fastener of diaper "L" | 19.3 |
|  | Mechanical fastener 27 of Example 13 of the present invention | 14.1 |

Example 15

Figure 11:
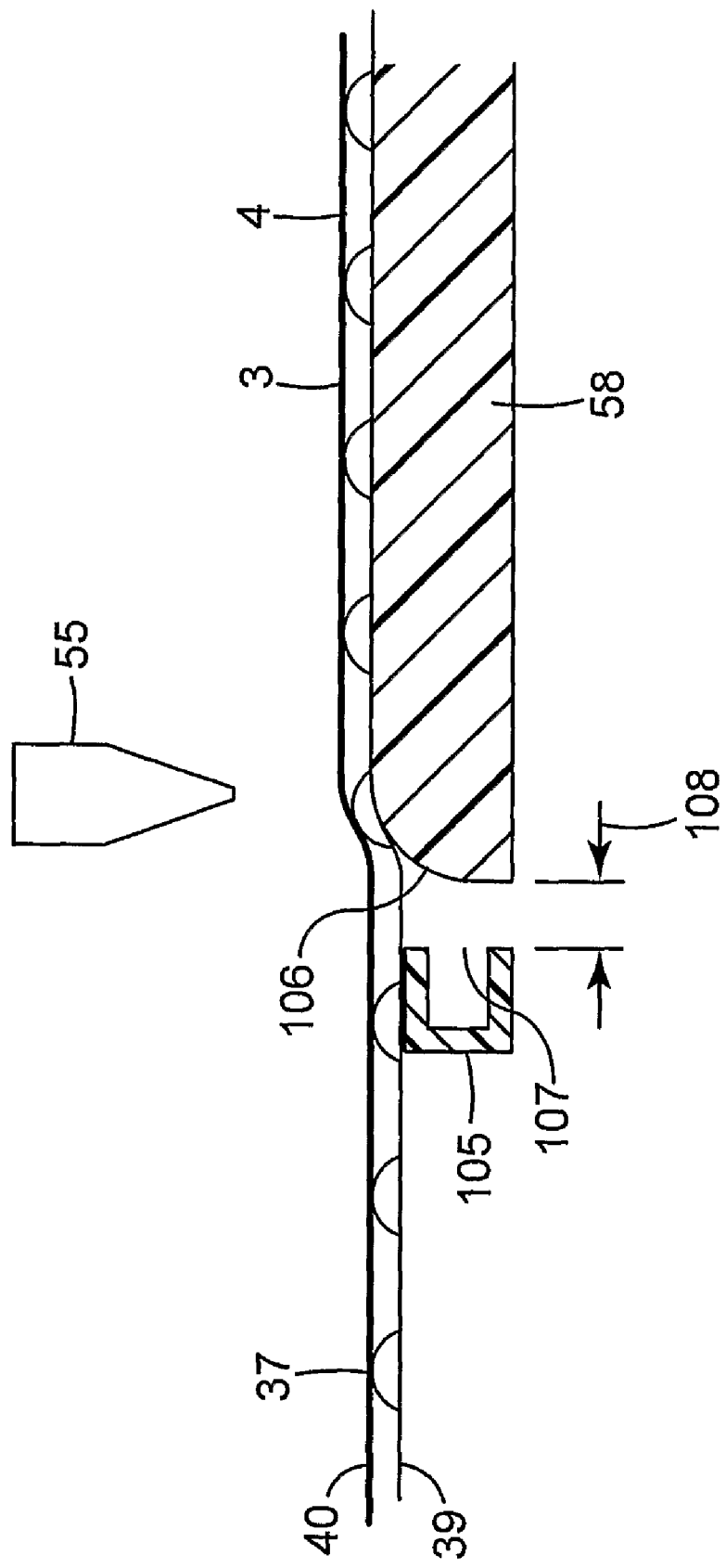
FIG. 11 is a schematic side sectional view of an alternative apparatus for manufacturing a fastener of the invention.

Method for Forming a Fastener. Reference is Made to the FIGS. 10 and 11

Using the second embodiment method, of the invention, granules of a high density polyethylene powder, available from Rowak AG under the trade name "Rowalit N-lOO-6 80-200 microns", were provided, as polymer particles 36. These polymer powders had a nominal size range of 80 to 200 microns a melt flow rate of 6 to 8 grams per 10 minutes. The surface energy of the polymer of the particles was about 31 mJ/m$^2$. As a sheet form base 4, a monolayer polyethylene film sheet, of 30 microns in thickness, was used, the sheet being a 30 percent to 70 percent mixture (blend) of a first and a second polyethylene. The first polyethylene was a high density bimodal polyethylene available from TVK rt under the trade name Tipelin 8000F and had the following parameters: a melt flow rate of 6 grams per 10 minutes (21.6 kg/190° C.), a density of 0.945-0.951 g/cm$^3$, and Shore D hardness 61. The second grade was a high density polyethylene available from TVK rt under the trade name Tipelin FS 471-02 and had the following parameters: a melt flow rate of 0.18 grams per 10 minutes, a density of 0.947 g/cm$^3$. As a release surface 40 a contact release surface, made of the "Chemglas" brand PTFE-coated glass fibre web used in Example 1 except that it was a black antistatic. The release conveyor 39 is driven around two drive rollers 11. Therebetween, the release surface 40 is kept horizontal. The base 4, was annealed as described in Example 12 above. The horizontal release surface 40 is kept at a temperature of about 100° C. at the place where the polymer particles 36 are scattered. Downstream of the scattering location the release surface 40 was heated to a temperature of at least about 180° C. The heating was provided by a hot plate 24 under the release conveyor 39. The polymer particles 36 were dispersed with a scatter unit 42. The height of the free fall of the polymer particles 36 from the scatter unit 42 to the release surface 40 was kept at about 30 mm. Almost every particle stays separate from the others, thus separate preform projections 37, sitting on and projecting from the release surface 40 to corresponding terminal ends 46, are formed. The particles are heated by the heat of the release surface 40, and thereby kept melted, i.e., in a semiliquid state. About 30 seconds after the polymer particles 36 getting to the release surface 40, they form preform projections 37 having acute contact angles 7, along their edges 12 contacting the release surface 40. In about 30 seconds from the particles getting to the release surface 40, the preform projections 37 form desired acute contact angles. Almost every particle remains separate, however, some of them melt together with their neighbour, forming "merged projections". Then the release surface 40 is cooled down to, and kept at, a temperature of about 72° C. An aluminium plate 58 of controlled temperature was provided under the release conveyor 39. The preform projections 44 were solidified and were suitable for contacting them with the front surface 20 of the base 4. The pre-treated base 57 was laid over the release surface 40, with the preform projections 37. The front surface 20 of the base 4 contacted the terminal ends 46 of the preform projections 37, i.e., the tops of the semi-lenticular, solidified droplets. A hot air nozzle 55 was fixed 10 mm above the back surface 3 of the base 4. The gap of the nozzle 55 was set in the crosswise direction. The gap size was 300 mm in length and 4 mm in width. As hot gas 21, air of a measured temperature of 499° C. was ejected onto the back surface 3 of the base 4 while the release conveyor 39 and the base 4 were kept together in a motion of a lateral direction 25. The dynamic pressing force of the air stream of the gap of the nozzle 55 was measured 10 mm under the gap, to be 2.32 grams per cm gap length. The speed of the release conveyor 39 was kept at 2.9 meters/minute. A vacuum device 105 (a rectangular chamber 75 cm long by 5 cm wide by 4.6 mm thick having a gap opening 107 of 1.6 mm in height and 50 cm in length starting adjacent the terminal end of the vacuum device) was connected to the inlet port of a fan (ELMO-G 2BH1 from Siemens Nash-Elmo, Germany) shown in FIG. 11, was positioned underneath the conveyor and was approximately 1-2 mm from the downstream rounded front edge 106 of the aluminum plate 58. The vacuum was adjusted by moving the vacuum chamber in relation to the aluminum plate until the release surface 40 was smooth and essentially wrinkle free. The terminal ends 46 also melted from the heat, to a suitable extent, thus fixing the terminal ends to the base with heat, i.e., fusing. Then everything was cooled down by air blower 1, whereby the base 4 regained its flat shape. The base 4, together with the engaging projections 13 fixed thereto, is separated and removed from the release surface 40, then wound up in a reel 38. The engaging projections 13 have flattened tops, overhanging the base 4 typically in all directions, and bordered all around, by an edge 12 whose average angle 2, essentially corresponded to the average contact angle 7.

The invention claimed is:

1. A fastener for engaging with a loop fabric, comprising a base having a front surface with a multiplicity of engaging projections at least some of the engaging projections having a top surface end, where the at least some engaging projections top surface ends form an edge angle surrounding the projections, and an attached end and a mantle surface extending from the top surface end edge to the attached end; at least one contour line of a side view of the mantle surface being strictly convex from a top surface edge to the attached end; wherein the at least some engaging projections are formed of a thermoplastic polymer.

2. The fastener for engaging with a loop fabric of claim 1 wherein the engaging projections are fixed to the base.

3. The fastener for engaging with a loop fabric of claim 2 wherein the engaging projections are fixed to the base by an adhesive layer on the base.

4. The fastener for engaging with a loop fabric of claim 1 wherein the engaging projection are formed of particles fused to the base.

5. The fastener for engaging with a loop fabric of claim 1 wherein the entire mantel surface is strictly convex.

6. The fastener for engaging with a loop fabric of claim 1 wherein the mantle surface is lenticular in shape.

7. The fastener for engaging with a loop fabric of claim 1 wherein the mantle surface is essentially of a cup shape.

8. The fastener for engaging with a loop fabric of claim 1 wherein the at least some engaging projections top surfaces form an edge completely surrounding the engaging projections.

9. The fastener for engaging with a loop fabric of claim 1 wherein the at least some engaging projections are substantially molecularly unoriented at least at the top surface.

10. The fastener for engaging with a loop fabric of claim 1 wherein the at least some engaging projections are substantially molecularly unoriented.

11. The fastener for engaging with a loop fabric of claim 1 wherein the attached end area is smaller than the top surface area.

12. The fastener for engaging with a loop fabric of claim 1 wherein the at least some engaging projections top surface ends are substantially flat.

13. The fastener for engaging with a loop fabric of claim 1 wherein the at least some engaging projections top surface ends are structured.

14. The fastener for engaging with a loop fabric of claim 1 wherein the at least some engaging projections form an edge angle of from 10 to 85 degrees.

15. The fastener for engaging with a loop fabric of claim 14 wherein the at least some engaging projections form an edge angle of from 30 to 80 degrees.

16. The fastener for engaging with a loop fabric of claim 1 wherein the at least some engaging projections are randomly distributed on the front surface of the base.

17. The fastener for engaging with a loop fabric of claim 1 wherein the at least some engaging projections are of random sizes and/or shapes.

18. The fastener for engaging with a loop fabric of claim 1 wherein the at least some engaging projections have sharp radii of curvature at the edges.

19. The fastener for engaging with a loop fabric of claim 1 wherein the at least some engaging projections are formed of a first material and the front surface of the base is formed of a second material different in some property than the first material.

20. The fastener for engaging with a loop fabric of claim 1 wherein the at least some engaging projections first material is a different polymer than the second material forming the front surface of the base.

21. The fastener for engaging with a loop fabric of claim 1 wherein the base is a polymer film.

22. The fastener for engaging with a loop fabric of claim 21 wherein the base is a multilayer polymer film.

23. The fastener for engaging with a loop fabric of claim 1 wherein the base is roughened.

24. The fastener for engaging with a loop fabric of claim 23 wherein the base is roughened by embossing.

25. The fastener for engaging with a loop fabric of claim 1 wherein the base is 5 to 100 microns thick.

26. The fastener for engaging with a loop fabric of claim 1 wherein the fastener base is a nonwoven.

27. The fastener for engaging with a loop fabric of claim 1 wherein the base is heat shrinkable.

28. The fastener for engaging with a loop fabric of claim 27 wherein the base has a heat shrinkability in a machine direction of at least 1%.

29. The fastener for engaging with a loop fabric of claim 1 wherein the base has a heat shrinkability in a cross direction of less than 50%.

30. The fastener for engaging with a loop fabric of claim 1 wherein the base has a heat shrinkability in cross direction which is lower than the heat shrinkability in machine direction.

31. The fastener for engaging with a loop fabric of claim 1 wherein the engaging projections are formed of at least two different particles.

32. The fastener for engaging with a loop fabric of claim 1 wherein the at least some engaging projections are formed of a rigid polymer.

33. The fastener for engaging with a loop fabric of claim 1 wherein at least some neighboring engaging projections are merged along adjacent side edges, forming a merged engaging projection.

34. The fastener for engaging with a loop fabric of claim 1 wherein the at least some engaging projections have no stem.

35. The fastener for engaging with a loop fabric of claim 1 wherein the at least some engaging projections edges have a perimeter of the edge line where the ratio of the average value of such perimeter to the average height of the projections is from 4.5 to 20.

36. The fastener for engaging with a loop fabric of claim 1 wherein the at least some engaging projections top surfaces have an area and the attached end has an area where it is attached to the front surface of the base where the ratio of the average top surface area to the average attached end area of the attached end is from 1.56 to 25.

37. The fastener for engaging with a loop fabric of claim 1 wherein the at least some engaging projections have a volume of from 0.0000335 mm$^3$ to 33.5 mm$^3$.

38. A fastener for engaging with a loop fabric, comprising a sheet-form base having a front surface with a multiplicity of randomly distributed engaging projections having a top surface end and an attached end attached to the front surface, wherein at least some neighboring engaging projections are merged along adjacent side edges, forming a merged engaging projection; and
wherein the at least some engaging projections are formed of a thermoplastic polymer.

39. The fastener for engaging with a loop fabric of claim 38 wherein the engaging projections are fixed to the base.

40. The fastener for engaging with a loop fabric of claim 39 wherein the engaging projections are fixed to the base by an adhesive layer on the base.

41. The fastener for engaging with a loop fabric of claim 38 wherein the engaging projection is formed of particles fused to the base.

42. A fastener for engaging with a loop fabric, comprising a sheet-form base having a front surface with a multiplicity of engaging projections at least some of the engaging projections having a top surface end and an attached end, which attached end is fused to the front surface of the base and the top surface forming an edge at least partially surrounding the projection; and
a mantle surface extending from the top surface end edge to the attached end; at least one contour line of a side view of the mantle surface being strictly convex from the top surface edge to the attached end;
wherein the at least some engaging projections are formed of a thermoplastic polymer.

43. The fastener for engaging with a loop fabric of claim 42 wherein the entire mantel surface is strictly convex.

44. The fastener for engaging with a loop fabric of claim 42 wherein the mantle surface is lenticular in shape.

45. The fastener for engaging with a loop fabric of claim 42 wherein the mantle surface is essentially of a cup shape.

46. The fastener for engaging with a loop fabric of claim 42 wherein the at least some engaging projections top surfaces form an edge completely surrounding the engaging projections.

47. The fastener for engaging with a loop fabric of claim 42 wherein the at least some engaging projections are substantially molecularly unoriented at least at the top surface.

48. The fastener for engaging with a loop fabric of claim 42 wherein the at least some engaging projections are substantially molecularly unoriented.

49. The fastener for engaging with a loop fabric of claim 42 wherein the attached end area is smaller than the top surface area.

50. The fastener for engaging with a loop fabric of claim 42 wherein the at least some engaging projections top surface ends are substantially flat.

51. The fastener for engaging with a loop fabric of claim 42 wherein the at least some engaging projections top surface ends are structured.

52. The fastener for engaging with a loop fabric of claim 42 wherein the at least some engaging projections form an edge angle of from 10 to 85 degrees.

53. The fastener for engaging with a loop fabric of claim 52 wherein the at least some engaging projections form an edge angle of from 30 to 80 degrees.

54. The fastener for engaging with a loop fabric of claim 42 wherein the at least some engaging projections are randomly distributed on the front surface of the base.

55. The fastener for engaging with a loop fabric of claim 42 wherein the at least some engaging projections are of random sizes and/or shapes.

56. The fastener for engaging with a loop fabric of claim 42 wherein the at least some engaging projections have sharp radii of curvature at the edges.

57. The fastener for engaging with a loop fabric of claim 42 wherein the at least some engaging projections are formed of a first material and the front surface of the base is formed of a second material different in some property than the first material.

58. The fastener for engaging with a loop fabric of claim 42 wherein the at least some engaging projections first material is a different polymer than the second material forming the front surface of the base.

59. The fastener for engaging with a loop fabric of claim 42 wherein the base is a polymer film.

60. The fastener for engaging with a loop fabric of claim 59, wherein the base is a multilayer polymer film.

61. The fastener for engaging with a loop fabric of claim 42 wherein the base is roughened.

62. The fastener for engaging with a loop fabric of claim 61 wherein the base is roughened by embossing.

63. The fastener for engaging with a loop fabric of claim 42 wherein the base is 5 to 100 microns thick.

64. The fastener for engaging with a loop fabric of claim 42 wherein the fastener base is a nonwoven.

65. The fastener for engaging with a loop fabric of claim 42 wherein the base is heat shrinkable.

66. The fastener for engaging with a loop fabric of claim 65 wherein the base has a heat shrinkability in a machine direction of at least 1%.

67. The fastener for engaging with a loop fabric of claim 42 wherein the base has a heat shrinkability in a cross direction of less than 50%.

68. The fastener for engaging with a loop fabric of claim 42 wherein the base has a heat shrinkability in cross direction which is lower than the heat shrinkability in machine direction.

69. The fastener for engaging with a loop fabric of claim 42 wherein the engaging projections are formed of at least two different particles.

70. The fastener for engaging with a loop fabric of claim 42 wherein the at least some engaging projections are formed of a rigid polymer.

71. The fastener for engaging with a loop fabric of claim 42 wherein at least some neighboring engaging projections are merged along adjacent side edges, forming a merged engaging projection.

72. The fastener for engaging with a loop fabric of claim 42 wherein the at least some engaging projections have no stem.

73. The fastener for engaging with a loop fabric of claim 42 wherein the at least some engaging projections edges have a sharp perimeter of the edge line where the ratio of the average value of such perimeter to the average height of the projections is from 4.5 to 20.

74. The fastener for engaging with a loop fabric of claim 42 wherein the at least some engaging projections top surfaces have an area and the attached end has an area where it is attached to the front surface of the base where the ratio of the average top surface area to the average attached end area of the attached end is from 1.56 to 25.

75. The fastener for engaging with a loop fabric of claim 42 wherein the at least some engaging projections have a volume of from 0.0000335 mm$^3$ to 33.5 mm$^3$.

76. A fastener for engaging with a loop fabric, comprising a sheet-form base having a front surface with a multiplicity of engaging projections at least some of the engaging projections having a top surface end and an attached end, which attached end is fixed to the front surface of the base by an adhesive layer on the base front surface and the top surface forming an edge at least partially surrounding the projection;
  where the at least some engaging projections top surface ends form an edge angle surrounding the projections, and a mantle surface extends from the top surface end edge to the attached end with at least one contour line of a side view of the mantle surface being strictly convex from a top surface edge to the attached end;
  wherein the at least some engaging projections are formed of a thermoplastic polymer.

77. The fastener for engaging with a loop fabric of claim 76 wherein the entire mantel surface is strictly convex.

78. The fastener for engaging with a loop fabric of claim 76 wherein the mantle surface is lenticular in shape.

79. The fastener for engaging with a loop fabric of claim 76 wherein the mantle surface is essentially of a cup shape.

80. The fastener for engaging with a loop fabric of claim 76 wherein the at least some engaging projections top surfaces form an edge completely surrounding the engaging projections.

81. The fastener for engaging with a loop fabric of claim 76 wherein the at least some engaging projections are substantially molecularly unoriented at least at the top surface.

82. The fastener for engaging with a loop fabric of claim 76 wherein the at least some engaging projections are substantially molecularly unoriented.

83. The fastener for engaging with a loop fabric of claim 76 wherein the attached end area is smaller than the top surface area.

84. The fastener for engaging with a loop fabric of claim 76 wherein the at least some engaging projections top surface ends are substantially flat.

85. The fastener for engaging with a loop fabric of claim 76 wherein the at least some engaging projections top surface ends are structured.

86. The fastener for engaging with a loop fabric of claim 76 wherein the at least some engaging projections form an edge angle of from 10 to 85 degrees.

87. The fastener for engaging with a loop fabric of claim 86 wherein the at least some engaging projections form an edge angle of from 30 to 80 degrees.

88. The fastener for engaging with a loop fabric of claim 76 wherein the at least some engaging projections are randomly distributed on the front surface of the base.

89. The fastener for engaging with a loop fabric of claim 76 wherein the at least some engaging projections are of random sizes and/or shapes.

90. The fastener for engaging with a loop fabric of claim 76 wherein the at least some engaging projections have sharp radii of curvature at the edges.

91. The fastener for engaging with a loop fabric of claim 76 wherein the at least some engaging projections are formed of a first material and the front surface of the base is formed of a second material different in some property than the first material.

92. The fastener for engaging with a loop fabric of claim 76 wherein the at least some engaging projections first material is a different polymer than the second material forming the front surface of the base.

93. The fastener for engaging with a loop fabric of claim 76 wherein the base is a polymer film.

94. The fastener for engaging with a loop fabric of claim 93, wherein the base is a multilayer polymer film.

95. The fastener for engaging with a loop fabric of claim 76 wherein the base is roughened.

96. The fastener for engaging with a loop fabric of claim 95 wherein the base is roughened by embossing.

97. The fastener for engaging with a loop fabric of claim 76 wherein the base is 5 to 100 microns thick.

98. The fastener for engaging with a loop fabric of claim 76 wherein the fastener base is a nonwoven.

99. The fastener for engaging with a loop fabric of claim 76 wherein the base is heat shrinkable.

100. The fastener for engaging with a loop fabric of claim 99 wherein the base has a heat shrinkability in a machine direction of at least 1%.

101. The fastener for engaging with a loop fabric of claim 76 wherein the base has a heat shrinkability in a cross direction of less than 50%.

102. The fastener for engaging with a loop fabric of claim 76 wherein the base has a heat shrinkability in cross direction which is lower than the heat shrinkability in machine direction.

103. The fastener for engaging with a loop fabric of claim 76 wherein the engaging projections are formed of at least two different particles.

104. The fastener for engaging with a loop fabric of claim 76 wherein the at least some engaging projections are formed of a rigid polymer.

105. The fastener for engaging with a loop fabric of claim 76 wherein at least some neighboring engaging projections are merged along adjacent side edges, forming a merged engaging projection.

106. The fastener for engaging with a loop fabric of claim 76 wherein the at least some engaging projections have no stem.

107. The fastener for engaging with a loop fabric of claim 76 wherein the at least some engaging projections edges have a perimeter of the edge line where the ratio of the average value of such perimeter to the average height of the projections is from 4.5 to 20.

108. The fastener for engaging with a loop fabric of claim 76 wherein the at least some engaging projections top surfaces have an area and the attached end has an area where it is attached to the front surface of the base where the ratio of the average top surface area to the average attached end area of the attached end is from 1.56 to 25.

109. The fastener for engaging with a loop fabric of claim 76 wherein the at least some engaging projections have a volume of from 0.0000335 mm$^3$ to 33.5 mm$^3$.

110. A method for forming a fastener, comprising:
providing a multiplicity of suitable thermoplastic particles;
providing a base with a front surface;
randomly dispersing and adhering, on the base front surface, the multiplicity of polymer particles thereby forming separate projections attached with their attachment ends at and projecting from the base front surface to corresponding terminal ends;
providing a deformation means having a contact surface;
contacting the terminal ends of the projections with the contact surface of the deformation means to heat the terminal ends above a softening temperature to deform the terminal ends so that they form a rim comprising an acute edge angle thereby forming engaging projections.

111. The method for forming a fastener of claim 110 wherein the base is cooled to a temperature to provide that the base front face and the projection ends adjacent the base front surface are stable.

112. The method for forming a fastener of claim 110 wherein the heated terminal ends are deformed to form a substantially flat surface with a edge having an acute edge angle (2).

113. The method according to claim 110, wherein at least some separate projections comprise exactly one polymer particle per projection.

114. The method according to claim 110 wherein at least some of the projections are provided with an acute edge angle (2) of between 30° and 80°.

115. A disposable diaper (10) comprising a bodyside liner and an outer surface, formed at least in part of a nonwoven fabric, the diaper having at least one side portion provided with a male mechanical fastener according to claim 1.

116. The disposable diaper (10) according to claim 115 where the non-woven fabric of the outer surface is a low loft fabric engagable with the fastener 43 of a size such that it provides a shear force of at least 4.9 N to the outer surface.

117. The disposable diaper of claim 116 wherein the mechanical fastener engagable with the low loft nonwoven fabric forming the diaper outer surface is a size such that it provides a shear force of at least 9.8 N to the outer surface.

118. The disposable diaper of claim 116 wherein the mechanical fastener engagable with the low loft nonwoven fabric forming the diaper outer surface provides a shear strength of at least 2.5 N/cm$^2$ to the outer surface.

119. The disposable diaper of claim 118 wherein the mechanical fastener engagable with the low loft nonwoven fabric forming the diaper outer surface provides a shear strength of at least 3.5 N/cm$^2$ to the outer surface.

* * * * *